United States Patent
Priel

(10) Patent No.: US 10,111,880 B2
(45) Date of Patent: Oct. 30, 2018

(54) COMPOUNDS FOR THE TREATMENT OF DIABETES AND DISEASE COMPLICATIONS ARISING FROM SAME

(71) Applicant: BEN-GURION UNIVERSITY OF THE NEGEV RESEARCH AND DEVELOPMENT AUTHORITY, Beer Sheva (IL)

(72) Inventor: Esther Priel, Beer Sheva (IL)

(73) Assignee: BEN-GURION UNIVERSITY OF THE NEGEV RESEARCH AND DEVELOPMENT AUTHORITY, Beer Sheva (IL)

( * ) Notice: Subject to any disclaimer, the term of this patent is extended or adjusted under 35 U.S.C. 154(b) by 0 days.

(21) Appl. No.: 15/034,303

(22) PCT Filed: Nov. 4, 2014

(86) PCT No.: PCT/IL2014/050959
§ 371 (c)(1),
(2) Date: May 4, 2016

(87) PCT Pub. No.: WO2015/068156
PCT Pub. Date: May 14, 2015

(65) Prior Publication Data
US 2016/0263124 A1    Sep. 15, 2016

Related U.S. Application Data

(60) Provisional application No. 61/900,240, filed on Nov. 5, 2013.

(51) Int. Cl.
| | | |
|---|---|---|
| *A61K 31/08* | (2006.01) | |
| *A61K 31/5377* | (2006.01) | |
| *A61K 31/055* | (2006.01) | |
| *A61K 31/05* | (2006.01) | |
| *A61K 31/075* | (2006.01) | |
| *A61K 31/09* | (2006.01) | |
| *A61K 31/137* | (2006.01) | |
| *A61K 31/4025* | (2006.01) | |
| *A61K 31/4545* | (2006.01) | |
| *A61K 31/496* | (2006.01) | |
| *A61K 45/06* | (2006.01) | |

(52) U.S. Cl.
CPC .......... *A61K 31/5377* (2013.01); *A61K 31/05* (2013.01); *A61K 31/055* (2013.01); *A61K 31/075* (2013.01); *A61K 31/08* (2013.01); *A61K 31/09* (2013.01); *A61K 31/137* (2013.01); *A61K 31/4025* (2013.01); *A61K 31/4545* (2013.01); *A61K 31/496* (2013.01); *A61K 45/06* (2013.01)

(58) Field of Classification Search
CPC .............. A61K 31/5377; A61K 31/055; A61K 31/4025; A61K 31/496; A61K 31/075; A61K 31/4545; A61K 31/05; A61K 45/06; A61K 31/09; A61K 31/137
See application file for complete search history.

(56) References Cited

U.S. PATENT DOCUMENTS

| | | | |
|---|---|---|---|
| 4,093,557 A | 6/1978 | Zecher | |
| 4,783,495 A | 11/1988 | Pastor et al. | |
| 4,835,202 A | 5/1989 | Pastor et al. | |
| 5,198,531 A | 3/1993 | Webber | |
| 5,243,018 A | 9/1993 | Kuze et al. | |
| 5,290,658 A | 3/1994 | Uenishi et al. | |
| 5,399,363 A | 3/1995 | Liversidge et al. | |
| 5,543,158 A | 8/1996 | Gref et al. | |
| 5,571,825 A | 11/1996 | Boschelli et al. | |
| 5,583,016 A | 12/1996 | Villeponteau et al. | |
| 5,625,027 A | 4/1997 | Kuze et al. | |
| 5,641,515 A | 6/1997 | Ramtoola | |
| 6,028,103 A | 2/2000 | Brugnara et al. | |
| 6,191,165 B1 | 2/2001 | Ognyanov et al. | |
| 6,331,564 B1 | 12/2001 | Brugnara et al. | |
| 6,380,378 B1 | 4/2002 | Kitamura et al. | |
| 6,399,738 B1 | 6/2002 | Ito | |
| 7,115,619 B2 | 10/2006 | Stevens et al. | |
| 7,846,904 B2 | 12/2010 | Harley et al. | |
| 8,604,245 B2 | 12/2013 | Priel et al. | |
| 8,609,736 B2 | 12/2013 | Gazit et al. | |
| 2002/0160939 A1 | 10/2002 | Michaeli | |
| 2004/0220186 A1 | 11/2004 | Bell et al. | |
| 2005/0049208 A1* | 3/2005 | Kaufmann | A23L 1/293 514/28 |
| 2006/0111365 A1 | 5/2006 | Tauchi | |
| 2007/0042962 A1 | 2/2007 | Adams et al. | |
| 2010/0267667 A1* | 10/2010 | Gazit | A61K 31/03 514/63 |

FOREIGN PATENT DOCUMENTS

| | | |
|---|---|---|
| EP | 0193256 A1 | 9/1986 |
| EP | 0397831 B1 | 9/1993 |
| EP | 0576357 A1 | 12/1993 |
| EP | 0604983 A1 | 7/1994 |
| EP | 0745600 A1 | 12/1996 |
| EP | 0658161 B1 | 7/1999 |
| EP | 1219609 A1 | 7/2002 |
| EP | 1112251 B1 | 5/2003 |
| EP | 1144395 B1 | 4/2005 |
| EP | 1183020 B1 | 8/2006 |
| EP | 2152663 B1 | 3/2014 |
| JP | 02121941 A | 5/1990 |
| JP | 10153884 A | 6/1998 |
| JP | 10273461 A | 10/1998 |

(Continued)

OTHER PUBLICATIONS

De Jesus et al (Aging Cell, 2011, 10, pp. 604-621).*

(Continued)

*Primary Examiner* — Sudhakar Katakam
(74) *Attorney, Agent, or Firm* — Lucas & Mercanti, LLP

(57) ABSTRACT

The present invention is directed to use of a series of tri-aryl compounds and compositions comprising the same for the treatment of diabetes and disease conditions arising as a consequence of the same.

22 Claims, 25 Drawing Sheets

(56) References Cited

FOREIGN PATENT DOCUMENTS

| | | |
|---|---|---|
| JP | 2005008626 A | 1/2005 |
| JP | 2006059694 A | 3/2006 |
| JP | 2007016214 A | 1/2007 |
| JP | 2001312055 A | 11/2011 |
| WO | 9315063 A1 | 8/1993 |
| WO | 9615784 A2 | 5/1996 |
| WO | 9731907 A1 | 9/1997 |
| WO | 9734589 A1 | 9/1997 |
| WO | 9734599 A2 | 9/1997 |
| WO | 9808871 A1 | 3/1998 |
| WO | 9835033 A1 | 8/1998 |
| WO | 9842691 A1 | 10/1998 |
| WO | 9961431 A1 | 12/1999 |
| WO | 0001495 A1 | 1/2000 |
| WO | 0018749 A1 | 4/2000 |
| WO | 0027848 A1 | 5/2000 |
| WO | 0034241 A1 | 6/2000 |
| WO | 0046209 A1 | 8/2000 |
| WO | 0104156 A1 | 1/2001 |
| WO | 0108677 A1 | 2/2001 |
| WO | 0121602 A1 | 3/2001 |
| WO | 01030771 A1 | 5/2001 |
| WO | 0140169 A1 | 6/2001 |
| WO | 0147935 A2 | 7/2001 |
| WO | 0149663 A2 | 7/2001 |
| WO | 0168603 A2 | 9/2001 |
| WO | 0213798 A2 | 2/2002 |
| WO | 02056880 A1 | 7/2002 |
| WO | 02059098 A1 | 8/2002 |
| WO | 02060422 A2 | 8/2002 |
| WO | 02100813 A2 | 12/2002 |
| WO | 03002531 A2 | 1/2003 |
| WO | 03004498 A1 | 1/2003 |
| WO | 03037432 A1 | 5/2003 |
| WO | 03059934 A2 | 7/2003 |
| WO | 03077949 A2 | 9/2003 |
| WO | 2006007864 A1 | 7/2004 |
| WO | 2004082667 A1 | 9/2004 |
| WO | 2005003129 A1 | 1/2005 |
| WO | 2005012485 A2 | 2/2005 |
| WO | 2005095381 A1 | 10/2005 |
| WO | 2005120514 A1 | 12/2005 |
| WO | 2006083869 A2 | 8/2006 |
| WO | 2006084031 A1 | 8/2006 |
| WO | 2008149346 A2 | 12/2008 |

OTHER PUBLICATIONS

MacAulay et al (Expert Opin.Ther.Targets, 2008, 12 (10), pp. 1265-1274).*

Extended European Search Report issued in related European Application No. 08763505.8, dated Oct. 10, 2011 (15 pages).

Xhan et al., "Clotrimazole and efaroxan stimulate insulin secretion by different mechanisms in rat pancreatic islets", Naunyn-Schmiedeberg's Arch Pharmacol, 1997, vol. 356, pp. 763-768.

Peterson et al., "Expanding the Scope of Crystal Form Evaluation in Pharmaceutical Science", J Pharm Pharmaceut Sci, 2006, vol. 9, No. 3, pp. 317-326.

Morissette et al., High-throughput crystallization: polymorphs, salts, co-crystals and solvates of pharmaceutical solids, Advanced Drug Delivery Reviews, 2004, vol. 56, pp. 275-300.

Rouhi, "The Right Stuff From research and development to the clinic getting drug crystals right is full of pitfalls." Chem. & Eng. News, 2003, vol. 81, No. 8, 13 pages.

Tichon et al., "Oxidative Stress Protection by Novel Telomerase Activators in Messenchymal Stem cells derived from Healthy and Diseased Individuals", Current Molecular Medicine 2013, 13, 1010-1022; 2013 Bentham Science Publishers, 13 pages.

Bernardes de Jesus, et al, "The telomerase activator TA-65 elongates short telomeres and increases healtj span of adult/old mice without increasing cancer incidence", Aging Cell Jul. 22, 2016; pp. 604-621, 18 pages.

International Search Report for International Application No. PCT/IL2014/050959 (dated Feb. 23, 2015)(2 pages).

Daniela Cihakova MD., Ph.D., "Type 1 Diabetes Mellitus", Johns Hopkins Medical Institutions Autoimmune Disease Research Center, 2001, Printout dated Jun. 18, 2015 from http:autoimmune.pathology.jhmi.edu/diseases.cfm?systemID=3&DiseaseID=23 (5 pages).

Lomakin et al., "Modem Polymer Flame Retardency", New Concepts in Polymer Science, 2003 (3 pages).

Canadian Examination Report for related Canadian Patent Application No. 2,690,004, dated Feb. 8, 2016 (3 pages).

West, "Solid State Chemistry and Its Applications," WILEY, 1988 (3 pages).

Dyker et al. "Sterically Stabilized p-Quinodimethanes by Nucleophilic Aromatic Substitution", European Journal of Organic Chemistry, vol. 2006, No. 9, 2006, pp. 2134-2144.

Eurasian Office Action dated Jan. 15, 2016, which is issued for related Eurasian Application No. 201401193/28 and is English translation (5 pages).

Neamati et al., "Depsides and depsidones as inhibitors of HIV-1 integrase: Discovery of Novel Inhibitors through 3D Database Searching," Journal of Medicinal Chemistry, American Chemical Society, 1997, vol. 40, No. 6, pp. 942-951.

N. Dessalew et al., "Investigation of potential glycogen synthase kinase 3 inhibitors using pharmacophore mapping and virtual screening", Chemical Biology & Drug Design, Blackwell Publishing TD., 2006, vol. 68, No. 3, pp. 154-165.

Pastor et al., "Organophosphorous and organosilicon derivatives of sterically hindered phenols", Journal of Organometallic Chemistry, 1989, vol. 376, No. 1, pp. 21-29.

B. Kirste et al., "Hydrogen-1 and Carbon-13 ENDOR investigations of sterically hindered galvinoxyl radicals", Journal of the American Chemical Society, 1981, vol. 103, No. 21, pp. 6280-6286.

M. E. Wacks et al., "Multiply charged ions", Recent Topics in Mass Spectrometry: Articles . . . From A Nato Study Institute of Mass Spectrometry, Gordon and Breach Science Publishers, 1971, pp. 1-9.

PCT International Search Report (as WO 2008/149345 A3) issued in related PCT Application No. PCT/IL2008/000747 filed Nov. 10, 2008 (2 pages).

Extended European Search Report issued in related European Application No. 08763505.8, Oct. 10, 2011 (15 pages).

Chan et al., "Clotrimazole and efaroxan stimulate insulin secretion by different mechanisms in rat pancreatic islets", Naunyn-Schmiedeberg's Arch Pharmacol, 1997, vol. 356, pp. 763-768.

"Diabetes Document" Johns Hopkins Medical Institutions, 2001, 5 pages.

Notice of Allowance, Applicant Initiated Interview Summary, and Notice of Allowability, including PTO-892 and AFCP 2.0 Decisiion dated Feb. 3, 2017 and issued in connection with U.S. Appl. No. 14/070,073 filed Nov. 12, 2013 (13 pages).

* cited by examiner

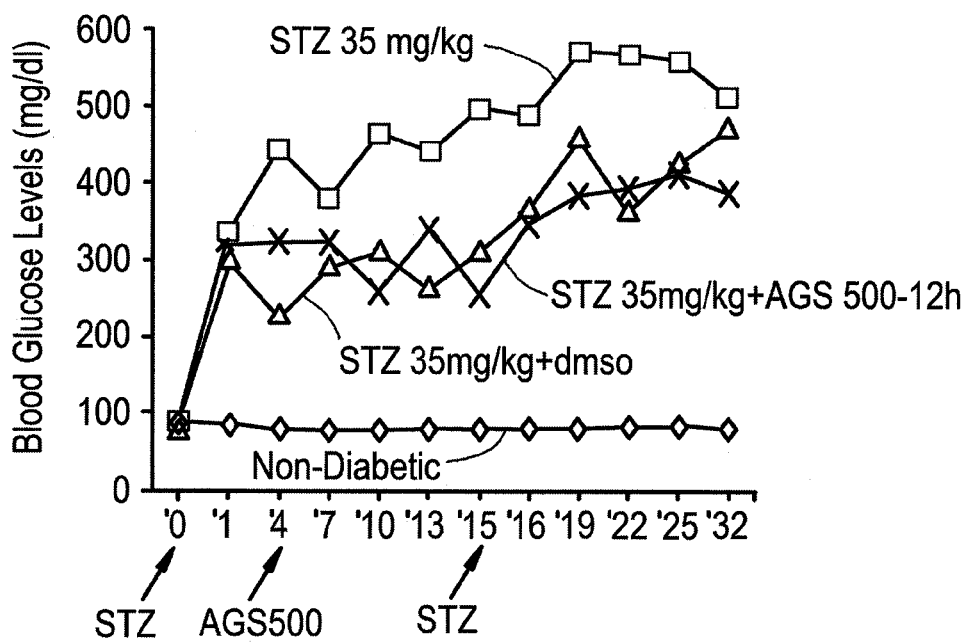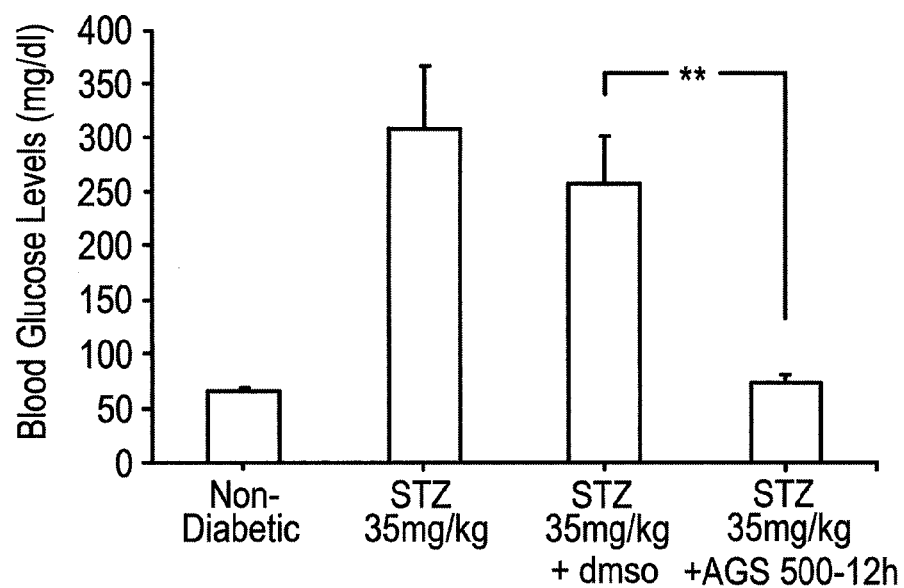

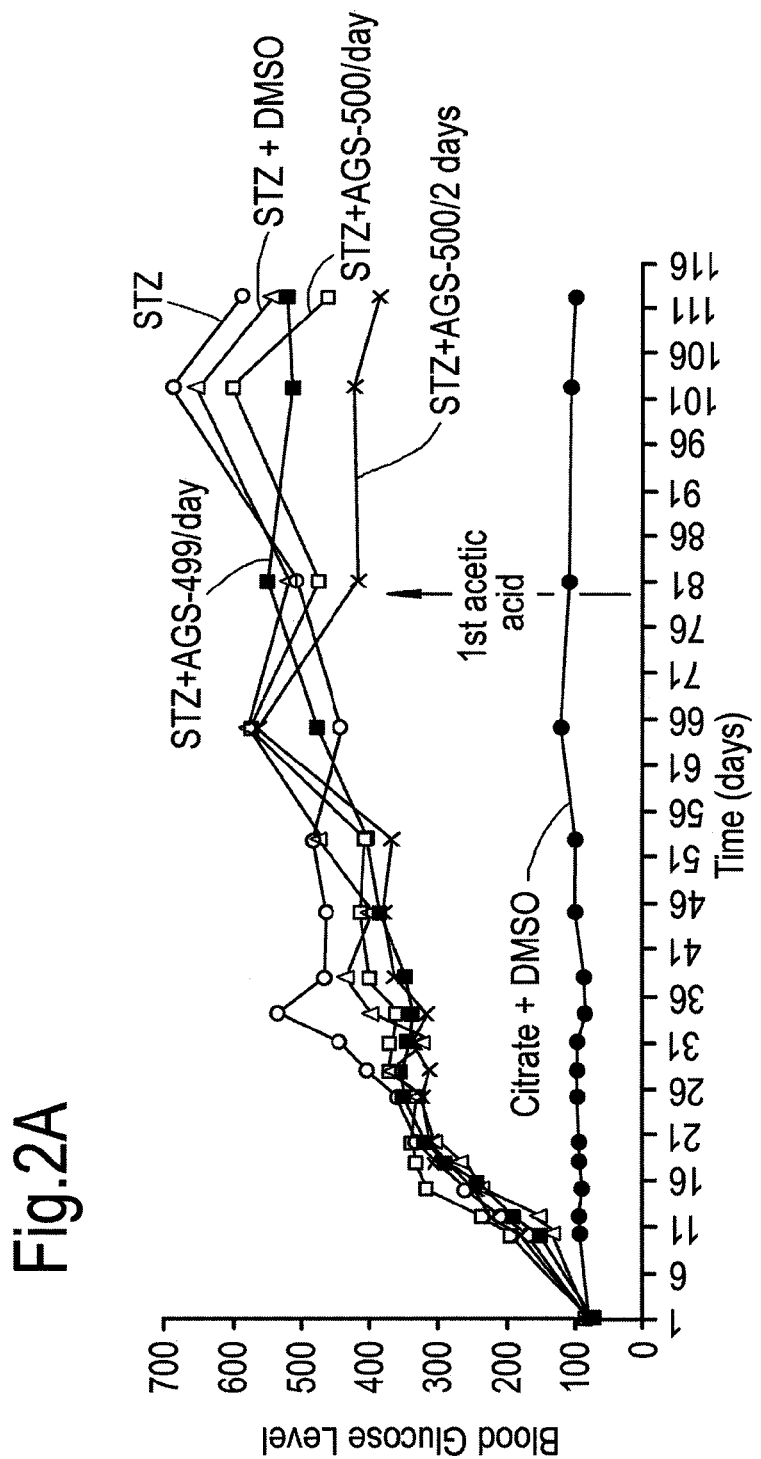

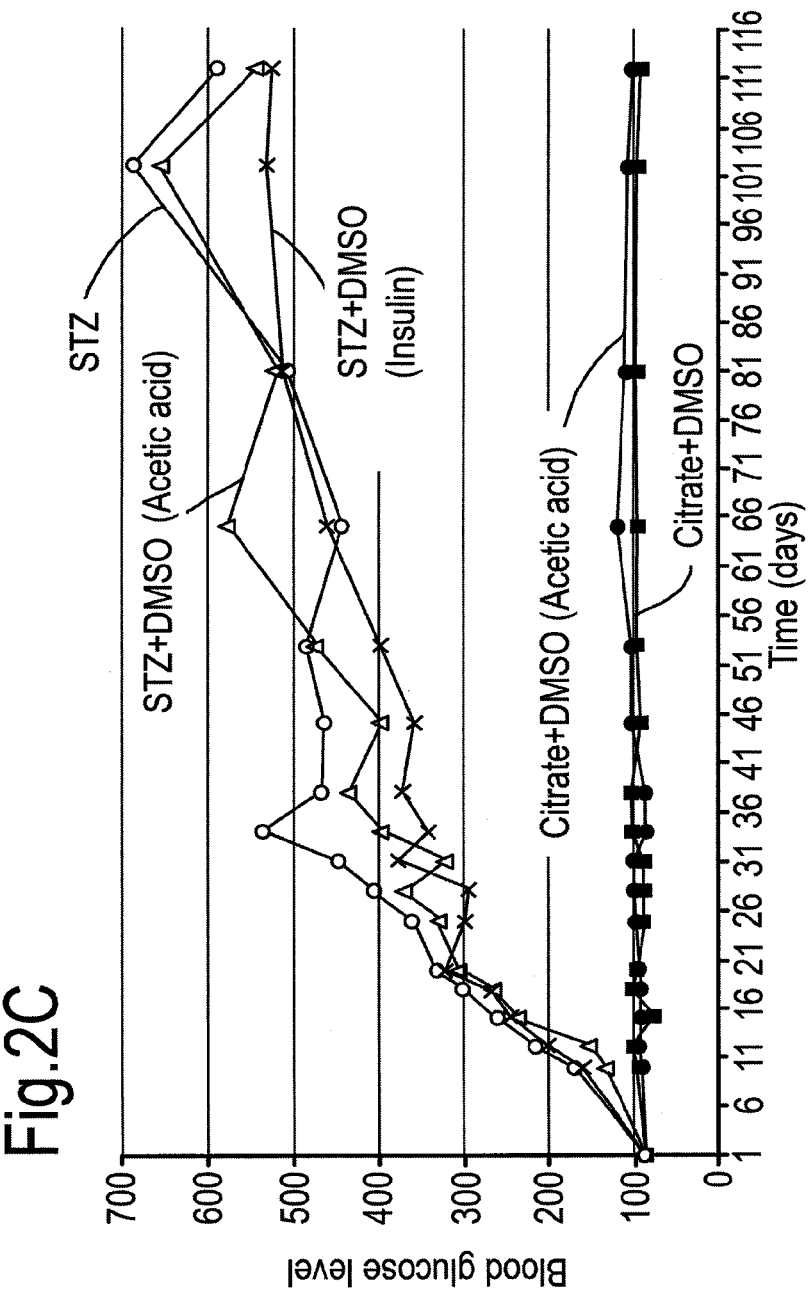

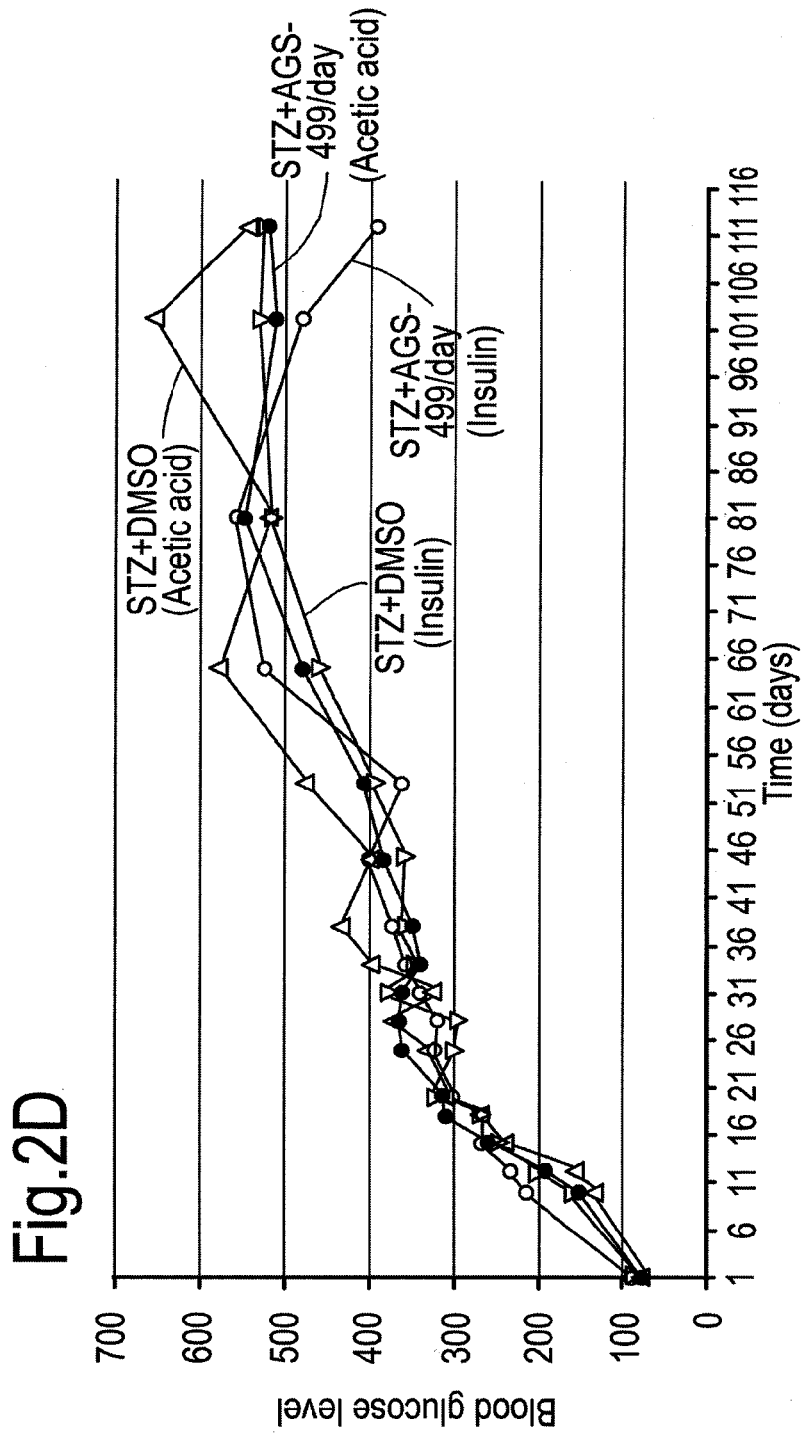

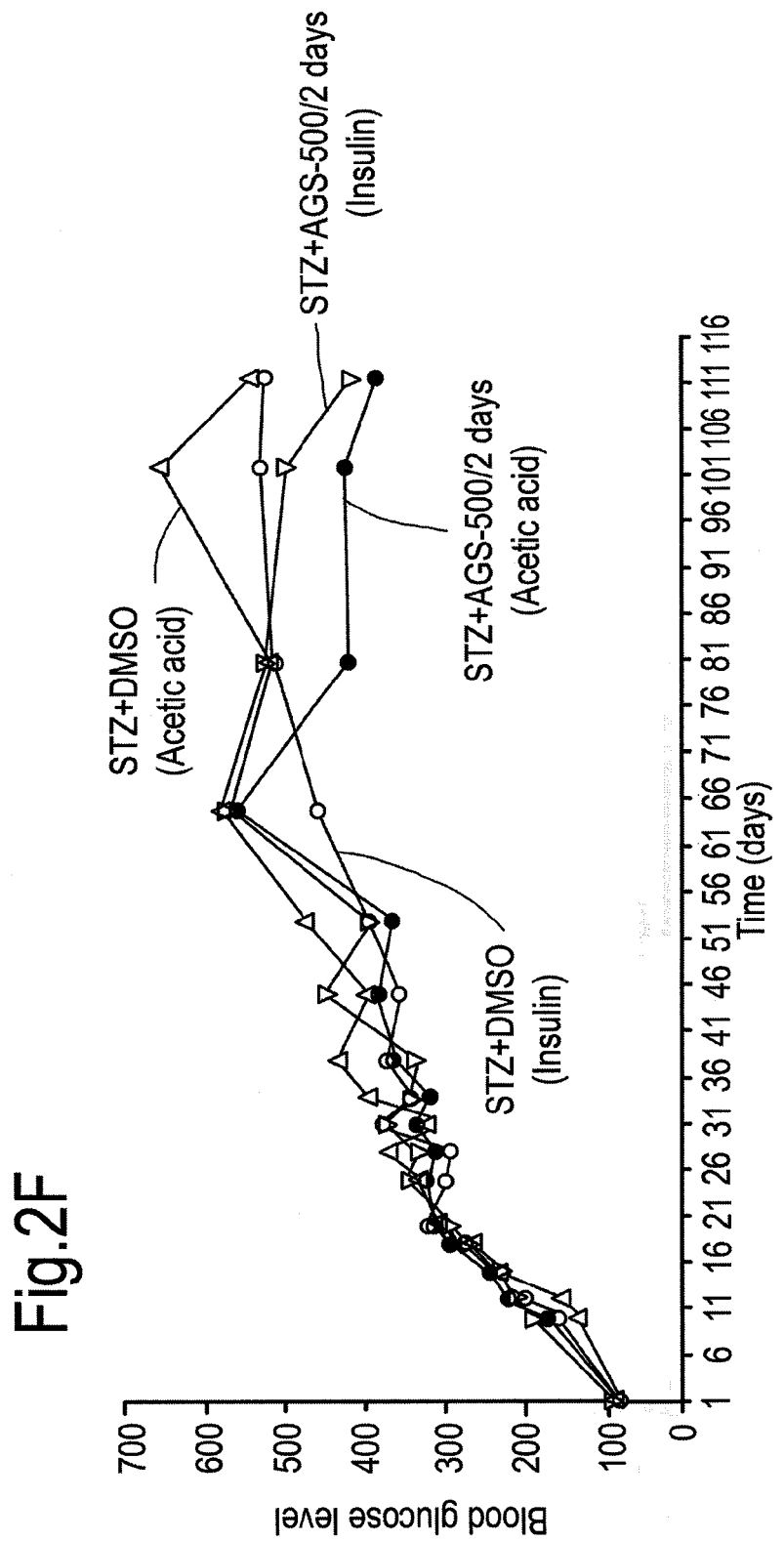

Fasting Glucose Levels
Acetic acid 1% (0.015% final)

Fasting Glucose Levels
Insulin (4U/Kg/2d)

Non-Diabetic

STZ 35mg/kg

STZ 35mg/kg + DMSO

STZ 35mg/kg + AGS 500-12h

Non-Diabetic

STZ35mg/kg

STZ 35mg/kg + DMSO

STZ 35mg/kg + AGS500-12h

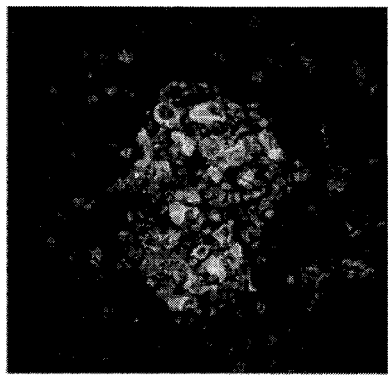
Fig.5C-1 Citrate + DMSO Acetic acid
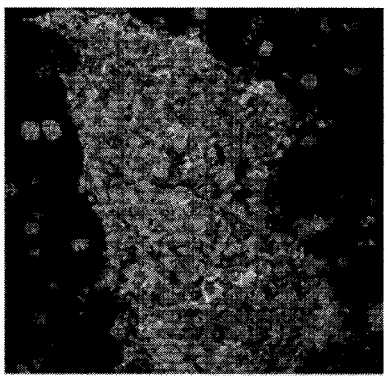
Fig.5C-4 Citrate + DMSO Insulin (4U/kg)
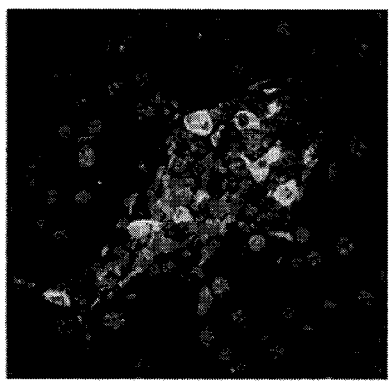
Fig.5C-2 STZ + DMSO Acetic acid
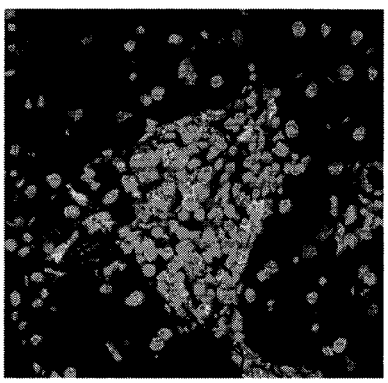
Fig.5C-5 STZ + DMSO Insulin (4U/kg)
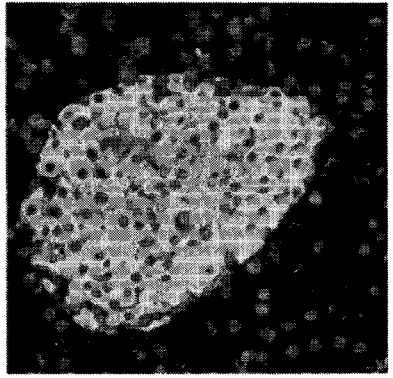
Fig.5C-3 STZ + AGS-500 Acetic acid
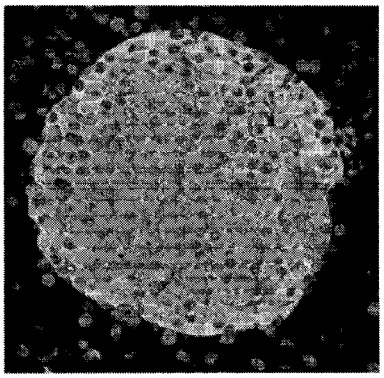
Fig.5C-6 STZ + AGS-500 Insulin (4U/kg)

Fig.5D (Rats)
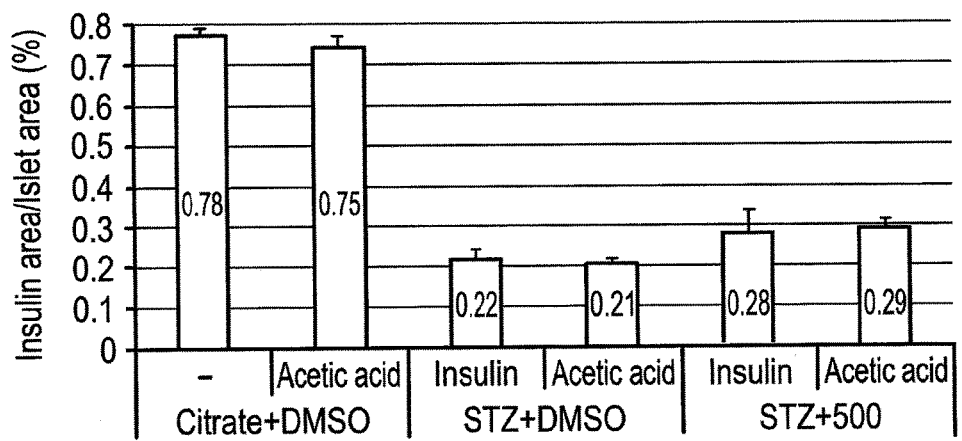
Fig.5E (Mice)

STZ+AGS500 50nM

STZ+DMSO

STZ

STZ+AGS500 250nM

STZ+AGS500 100nM

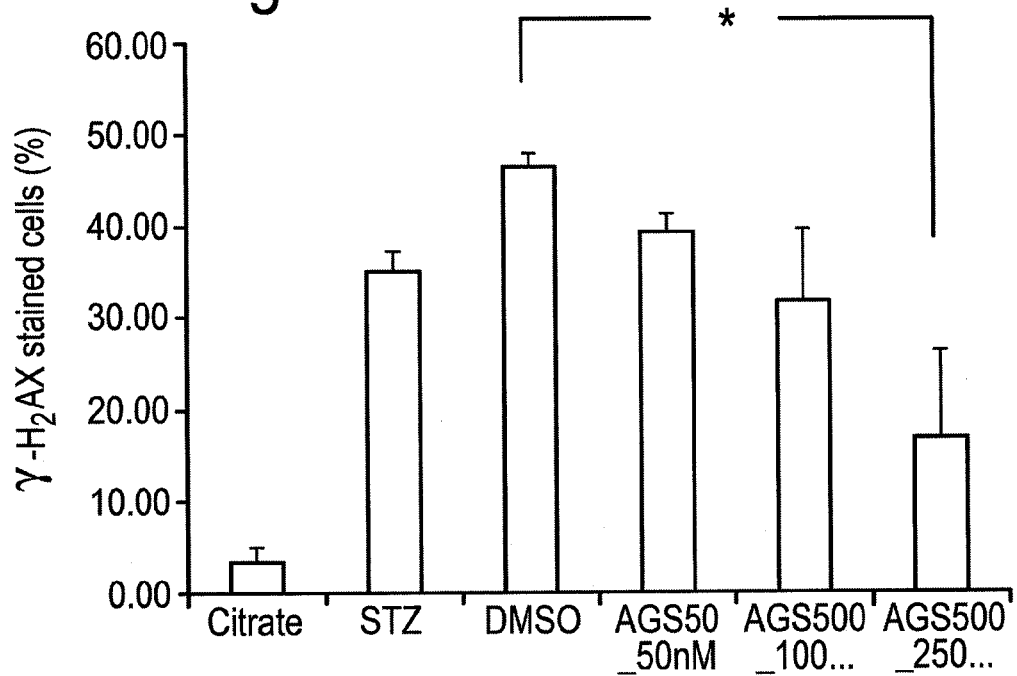
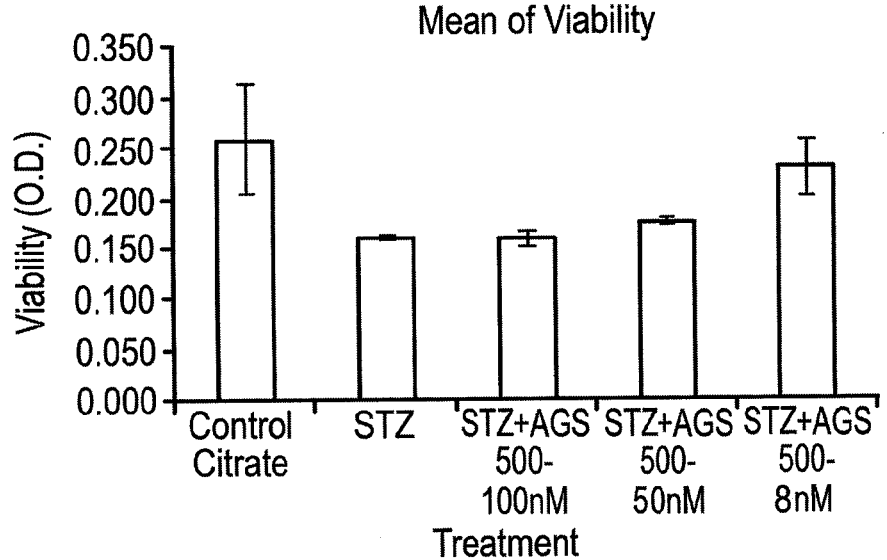

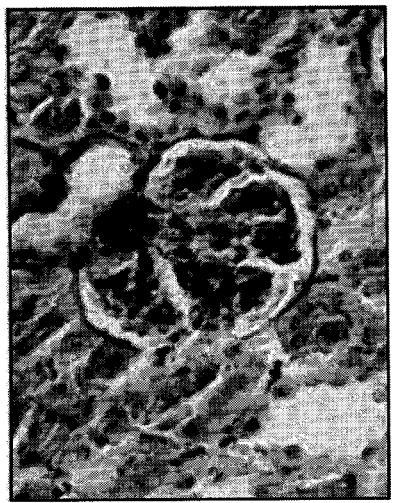
Fig.8-3 STZ + AGS
Fig.8-2 STZ
Fig.8-1 STZ+DMSO
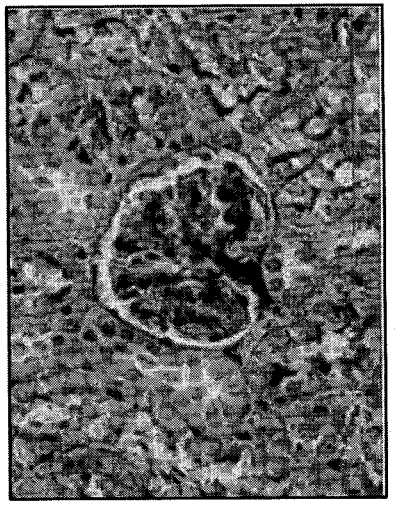
Fig.8-5 Citrate
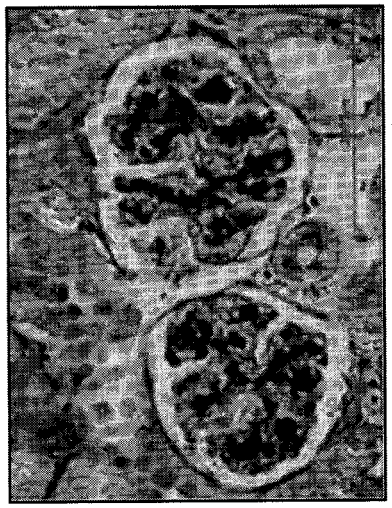
Fig.8-4 Citrate + DMSO

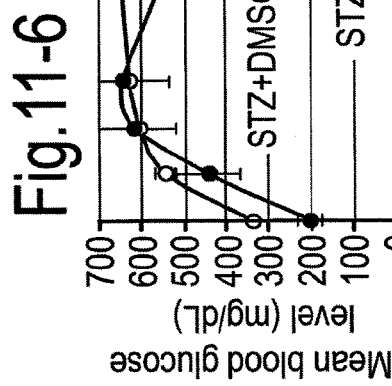
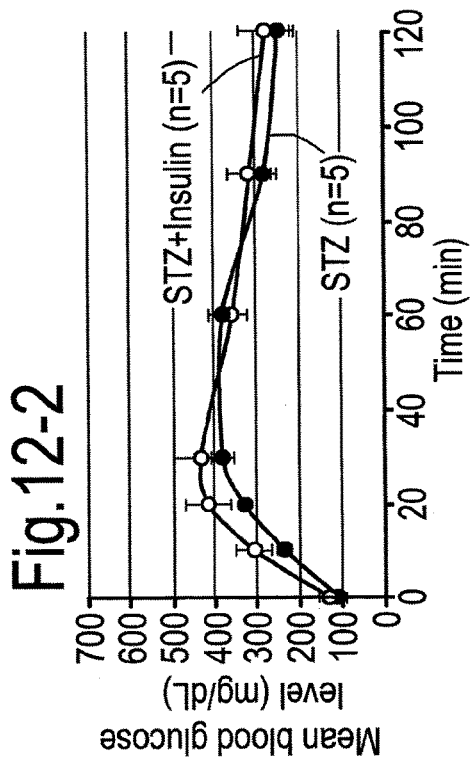
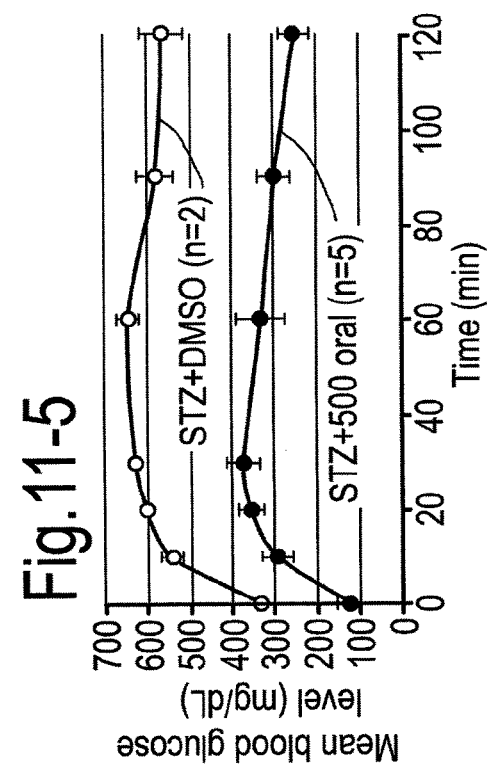
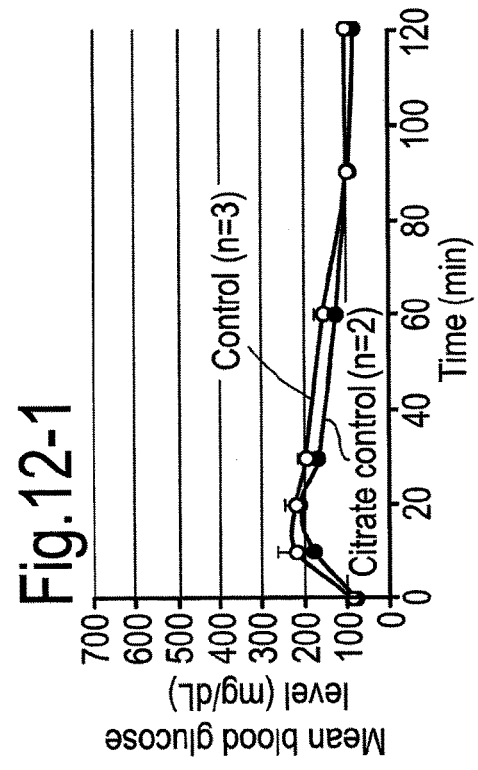

COMPOUNDS FOR THE TREATMENT OF DIABETES AND DISEASE COMPLICATIONS ARISING FROM SAME

CROSS-REFERENCE TO RELATED APPLICATIONS

This application is a 371 of PCT/IL2014/050959, filed Nov. 4, 2014, which claims the benefit of U.S. Patent Application No. 61/900,240, filed Nov. 5, 2013, the contents of each of which are incorporated herein by reference.

FIELD OF THE INVENTION

The present invention is directed to the use of a series of compounds and compositions comprising the same for treating diabetes and disease related complications thereof.

BACKGROUND OF THE INVENTION

Diabetes mellitus is one of the most prevalent metabolic disorders worldwide. Type 1 diabetes, most common among children and adolescents, accounts for approximately 10% of all diabetes cases. Type 2 diabetes afflicts over 7% of the adult population.

Type 1 diabetes is well recognized as an absolute insulin deficiency condition due to massive autoimmune destruction of pancreatic beta cells. Type 2 diabetes is characterized by several metabolic defects including beta cell dysfunction and reduction and peripheral insulin resistance.

While there are a number of available agents, which ameliorate diabetes, to date there is no cure for the disease.

SUMMARY OF THE INVENTION

In one embodiment, this invention provides a method of treating diabetes or diabetes related complications in a subject in need thereof, said method comprising administering to a subject a compound represented by the structure of formula I:

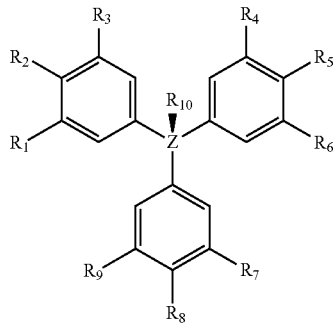

wherein
Z is carbon, nitrogen, phosphor, arsenic, silicon or germanium;
$R_1$ to $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido. alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$ forms a fused cycloalkyl, heterocycloalkyl, aromatic or heteroaromatic ring with the main aromatic ring; and
$R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof.

In one embodiment, this invention provides a method of reducing circulating glucose levels, reducing insulin resistance, stimulating or increasing insulin sensitivity, stimulating or increasing pancreatic beta-cell mass, or stimulating or increasing creatinine clearance in a subject in need thereof, or preventing or reducing renal damage in a diabetic subject in need thereof, said method comprising administering to a subject a compound represented by the structure of formula I:

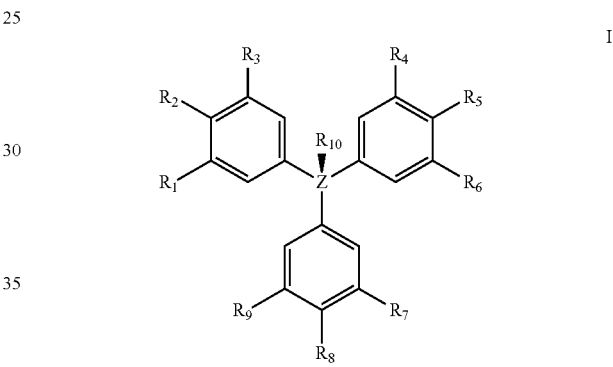

wherein
Z is carbon, nitrogen, phosphor, arsenic, silicon or germanium;
$R_1$ to $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido. alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and
$R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof.

In one embodiment the structure of formula I is represented by the structure of formula IV:

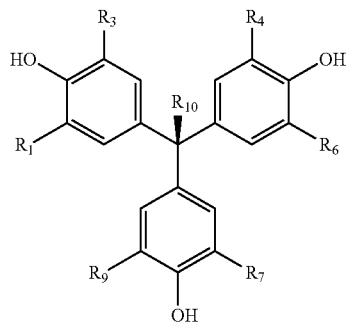

IV wherein $R_1$, $R_3$, $R_4$, $R_6$, $R_7$, $R_9$ and $R_{10}$ are as described above.

In another embodiment the structure of formula I is represented by the structure of formula VI:

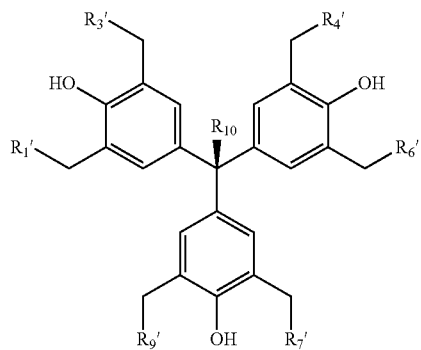

VI wherein $R_1'$, $R_3'$, $R_4'$, $R_6'$ $R_7'$, and $R_9'$ are the same or different comprising halogen, aryl, alkyl, cycloalkyl, heterocycloalkyl, alkoxy, monoalkylamino, dialkylamino or arylamino; and $R_{10}$ is as described above.

In another embodiment the structure of formula I is represented by the structure of formula VII:

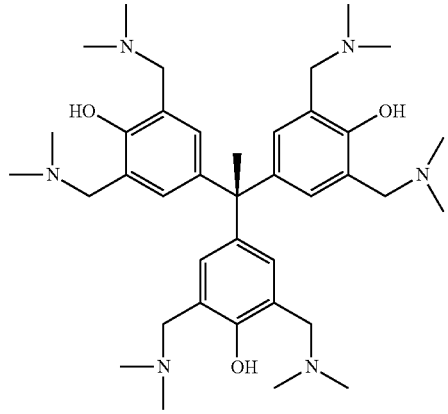

VII

In another embodiment the structure of formula I is represented by the structure of formula VIII:

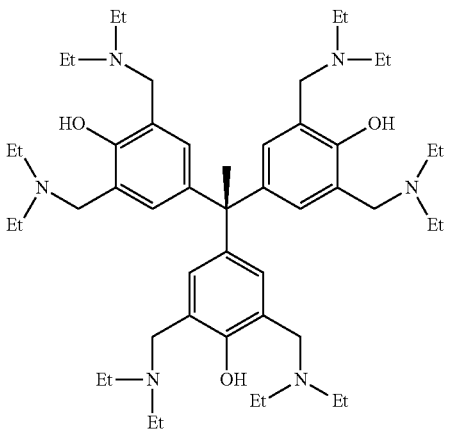

VIII

In another embodiment the structure of formula I is represented by the structure of formula IX:

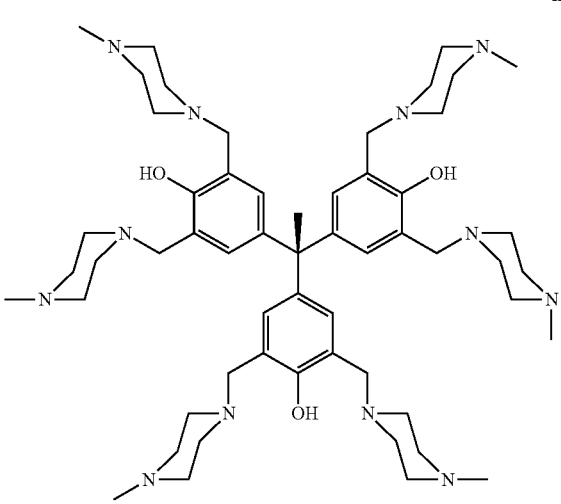

IX

In another embodiment the structure of formula I is represented by the structure of formula X:

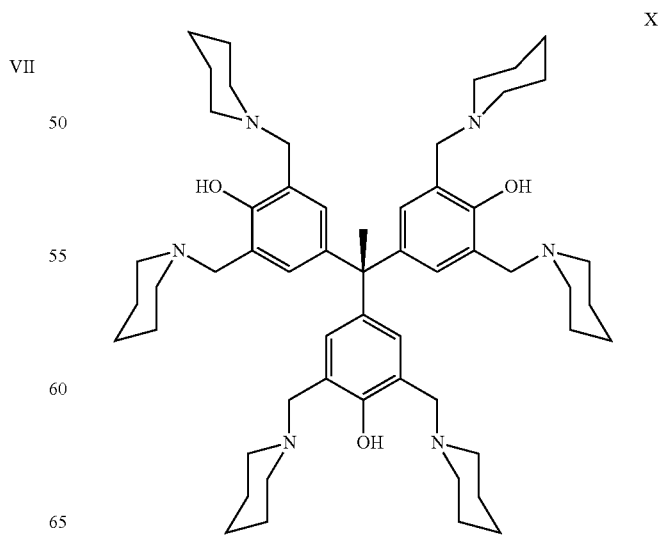

X

In another embodiment the structure of formula I is represented by the structure of formula XI:

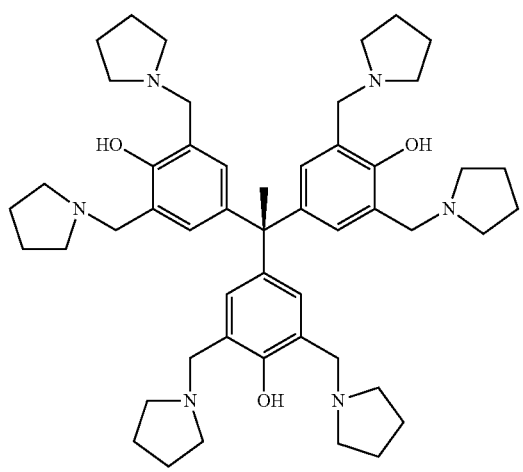

XI

In another embodiment the structure of formula I is represented by the structure of formula XII:

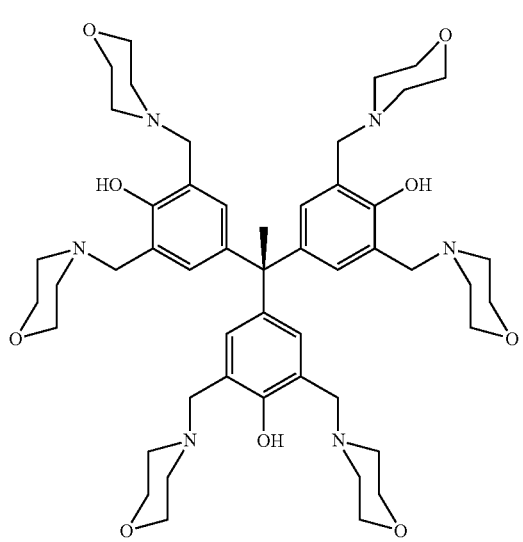

XII

In another embodiment the structure of formula I is represented by the structure of formula XIII:

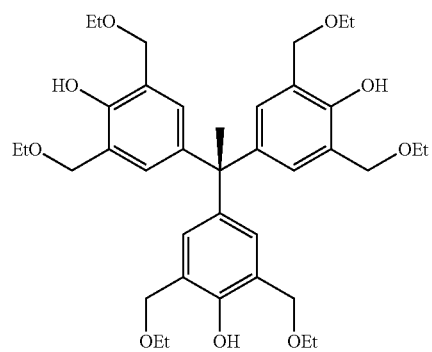

XIII

In another embodiment the structure of formula I is represented by the structure of formula XIV:

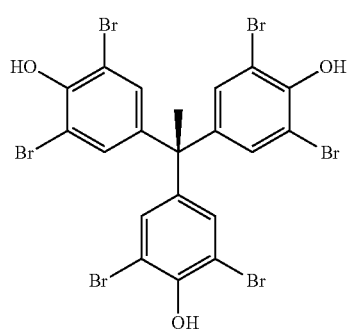

XIV

In another embodiment the structure of formula I is represented by the structure of formula XV:

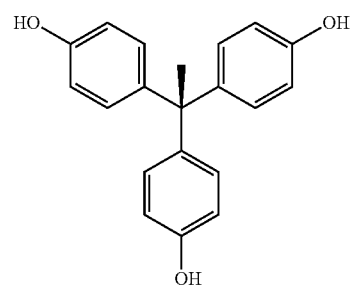

XV

In another embodiment the structure of formula I is represented by the structure of formula XVI:

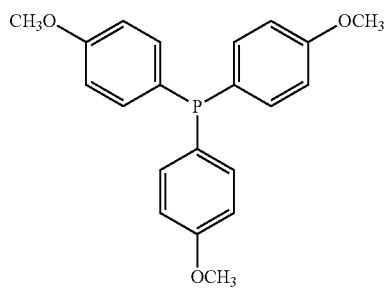

XVI

In another embodiment, the invention provides for the methods as herein described, wherein said subject is administered a second agent, which is useful in the treatment of diabetes or diabetes related complications.

According to this aspect, and in some embodiments, the subject is administered a second agent, which is useful in the reduction of circulating glucose levels, reduction of insulin resistance, stimulation or increase of insulin sensitivity, stimulation or increase of pancreatic beta-cell mass, or stimulation or increase of creatinine clearance in a subject, or prevention or reduction of renal disease in said subject.

In another embodiment, the invention provides for the use of a compound as described herein or a pharmaceutical composition comprising compounds as described herein for the preparation of a medicament for use in reducing circulating glucose levels, reducing insulin resistance, stimulating or increasing insulin sensitivity, stimulating or increasing pancreatic beta-cell mass, or stimulating or increasing creatinine clearance in a subject in need thereof, or preventing or reducing renal damage in a diabetic subject in need thereof. In some embodiments, the medicament may further comprise a second agent, which is useful in the treatment of diabetes or diabetes related complications. In some embodiments, the use may include such use by a subject who is diabetic, and receiving therapy with an alternate agent, which is useful in the treatment of diabetes or diabetes related complications.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1A: Reduction in Blood Glucose Level after 12 h Fast in AGS-500-treated Rats. Eight-week-old Wistar female rats received 2 injections of STZ (35 mg/kg) or citrate buffer at day 0' and day 15'. Rats were treated with AGS-500 or DMSO starting at day 4'. Blood glucose levels were measured every few days.

FIG. 1B Reduction in Blood Glucose Level after 12 h Fast in AGS-500-treated Rats. Eight-week-old Wistar female rats received 2 injections of STZ (35 mg/kg) or citrate buffer at day 0' and day 15'. Rats were treated with AGS-500 or DMSO starting at day 4'. Blood glucose levels were measured before sacrificing, after a 12 h fast (B). The results are mean±S.E.; n=4. **p<0.01.

FIG. 2A-FIG. 2F: Circulating Glucose levels in AGS treated mice versus controls over time, in animals given the indicated regimens, and noting insulin injections.

FIGS. 5A1-5A-4: AGS-500 Treatment Preserved β-cell Mass in STZ-Injected Rats. The pancreas was removed immediately after sacrificing, fixed in 4% formalin, and embedded in paraffin for immuno-histochemical and immuno-fluorescence staining using a specific anti-insulin antibody. Immunostaining shows greatest β-cell Mass in non-diabetic animals, while a dramatic reduction is seen in diabetic animals, which is restored in the AGS treated subject.

FIGS. 5B-1-5B-4, and FIGS. 5C-1-5C-6: Immunofluorescence studies show AGS-500 Treatment preserved β-cell Mass in STZ-injected rats (5B) and mice (5C), as well. The light grey (originally red) stains insulin producing cells, and the darker grey (originally blue) is for DAPI staining. Density of insulin staining per area was measured using "Image J" software (D-E). The results are mean±S.E.; n=4. ***p<0.005. Magnification: ×10.

FIGS. 5D (Rats) and 5E (Mice) plot the β-cell Mass density per area and insulin producing area per islet area, in the groups treated as indicated.

FIGS. 6A-1-6A-5: AGS-500 Treatment Reduced γ-H2AX Staining in Isolated Islets-Cells Treated with STZ. Islets were isolated from 8-10-week-old ICR mice. 30 islets in each group were treated with STZ (1.5 mM) and DMSO or AGS-500 in various concentrations (50 nM, 100 nM, 250 nM) for 4 hours. After 4 h incubation, the islets were enzymatically separated to single cells, cyto-spun and stained with γ-H2AX-specific antibody (A; representative picture—γ-H2AX (light grey), Dapi (dark grey)). Magnification: ×60.

FIG. 7A plots the number of stained cells from total cells in FIG. 6 was quantified. The results are mean±SE of 3 different experiments. *p<0.05.

FIG. 7B plots AGS-500 treatment effects on pancreatic beta cell viability.

FIGS. 8-1-8-5: AGS treatment reduces kidney damage arising following STZ-induced diabetes. PAS staining of kidney slices showing glomeruli derived from diabetic animals (designated STZ or STZ-DMSO) with and without AGS treatment. Representative sections are shown.

FIGS. 11-1-11-6 plots the results of a glucose tolerance test in terms of the mean circulating glucose levels in subjects administered AGS compounds for a short time course (2 weeks), showing improved results in diabetic mice administered the compounds as compared to vehicle treated diabetic mice.

FIGS. 12-1-12-6 plots the results of a glucose tolerance test in terms of the mean circulating glucose levels in subjects administered AGS compounds and insulin (added after the establishment of diabetes), for a short time course (2 weeks) Treatments with AGS compounds alone demonstrate similar results as AGS+insulin.

FIGS. 13-1-13-2 plots the mean circulating glucose levels in the diabetic state, when a short course of AGS treatment is compared to controls (FIG. 13-1), and further compared to co-administration of insulin (FIG. 13-2), as compared to controls.

DETAILED DESCRIPTION OF THE PRESENT INVENTION

Figure 2B:
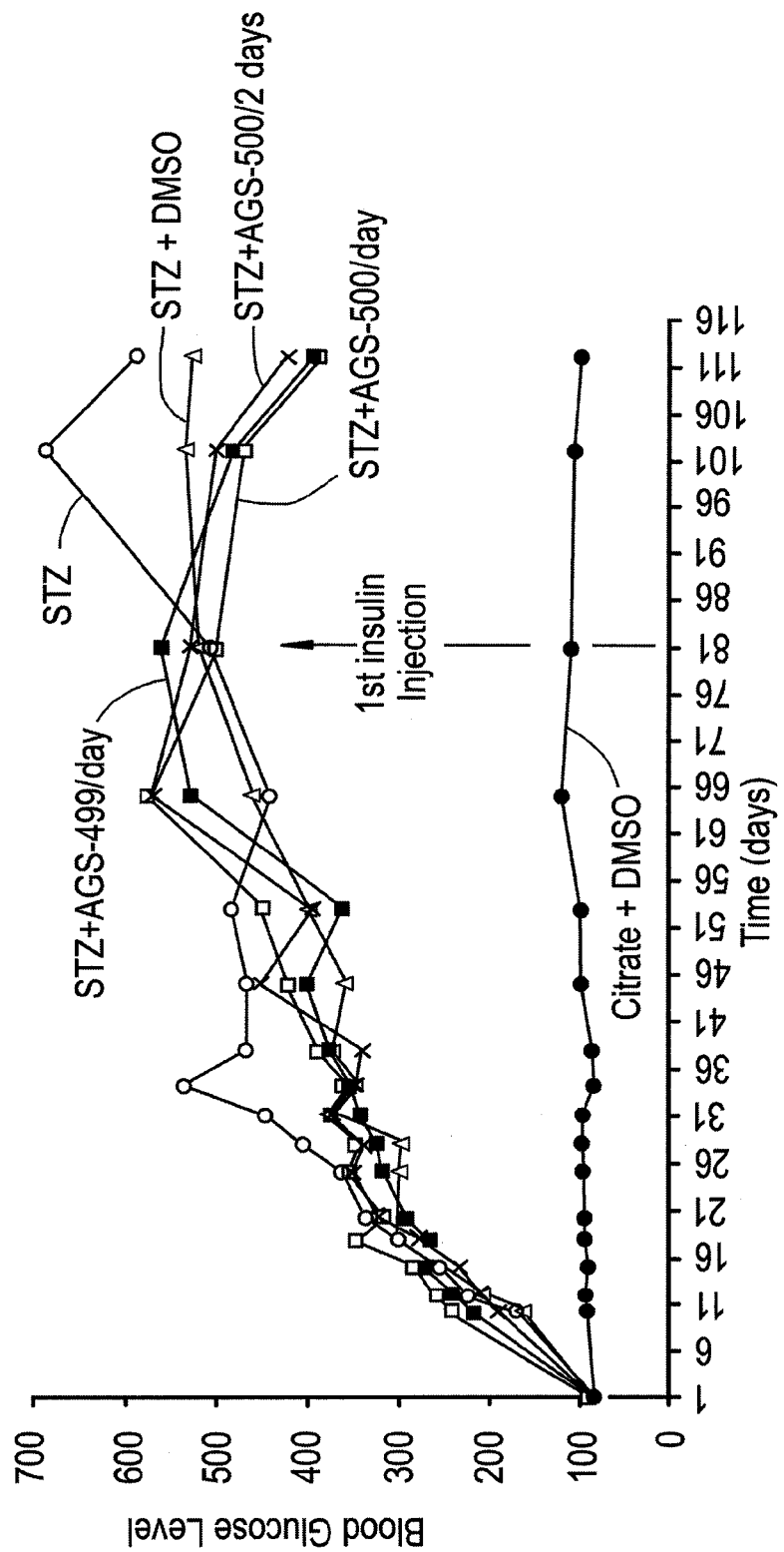

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The present invention relates, in some embodiments, to the use of a novel class of tri-phenyl compounds and compositions comprising the same for the treatment of, inter alia, diabetes and disease conditions related to diabetes.

In some embodiments, such disease complications specifically relate to kidney disease or in some embodiments, to diabetic neuropathy, or in some embodiments, diabetic retinopathy. For purposes of this application, however, disease conditions related to diabetes do not relate to diabetic skin disease/ulceration.

Compounds of the Invention:

In one embodiment, the methods of this invention comprise the use of tri-phenyl compounds represented by the structure of formula I:

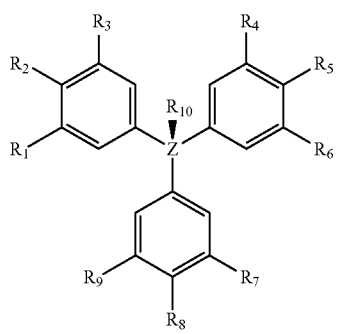

wherein
Z is carbon, nitrogen, phosphor, arsenic, silicon or germanium;
$R_1$ to $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido. alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula II:

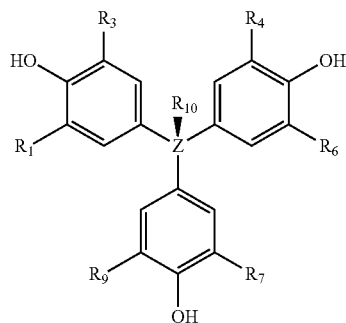

wherein
Z is carbon, nitrogen, phosphor, arsenic, silicon or germanium;
$R_1$, $R_3$, $R_4$, $R_6$, $R_7$ and $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido. alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and $R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof, and compositions comprising the same.

In one embodiment Z is carbon. In another embodiment $R_{10}$ is a methyl group. In another embodiment $R_1$, $R_3$, $R_4$, $R_6$, $R_7$, and $R_9$ are —$(CH_2)_n$-heterocycloalkyl group, wherein n is between 1-6. In another embodiment $R_1$, $R_3$, $R_4$, $R_6$, $R_7$, and $R_9$ are —$(CH_2)_n$-aminoalkyl group, wherein n is between 1-6. In another embodiment $R_1$, $R_3$, $R_4$, $R_6$, $R_7$, and $R_9$ are —$(CH_2)_n$-dialkylamino group, wherein n is between 1-6 In another embodiment $R_1$, $R_3$, $R_4$, $R_6$, $R_7$, and $R_9$ are —$(CH_2)n$-$N(CH_3)_2$ group, wherein n is between 1-6. In another embodiment $R_1$, $R_3$, $R_4$, $R_6$, $R_7$, and $R_9$ are —$(CH_2)_n$—$N(Et)_2$ group, wherein n is between 1-6. In another embodiment $R_1$, $R_3$, $R_4$, $R_6$, $R_7$, and $R_9$ are —$(CH_2)_n$-aryl group, wherein n is between 1-6. In another embodiment $R_1$, $R_3$, $R_4$, $R_6$, $R_7$, and $R_9$ are —$(CH_2)_n$-heteroaryl group, wherein n is between 1-6. In another embodiment $R_1$, $R_3$, $R_4$, $R_6$, $R_7$, and $R_9$ are —$(CH_2)_n$-haloalkyl group, wherein n is between 1-6. In another embodiment $R_1$, $R_3$, $R_4$, $R_6$, $R_7$, and $R_9$ are —$(CH_2)_n$-alkoxy group, wherein n is between 1-6. In another embodiment $R_1$, $R_3$, $R_4$, $R_6$, $R_7$, and $R_9$ are —$(CH_2)_n$-ethoxy group, wherein n is between 1-6. In another embodiment $R_1$, $R_3$, $R_4$, $R_6$, $R_7$, and $R_9$ are —$(CH_2)_n$-cycloalkyl group, wherein n is between 1-6.

In one embodiment, the methods of this invention comprise the use of tri-phenyl compounds represented by the structure of formula III:

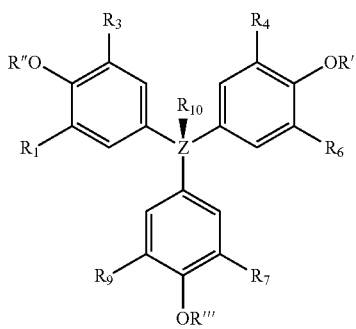

wherein
Z is carbon, nitrogen, phosphor, arsenic, silicon or germanium;
R', R" and R'" are independently the same or different comprising hydrogen, alkyl, haloalkyl, alkylamino, phenyl, benzyl, alkanyloyl, acetyl or benzoyl;
$R_1$, $R_3$, $R_4$, $R_6$, $R_7$ and $R_9$ are the same or different, H, D, OH, halogen, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, alkylalkoxy, haloalkyl, alkylhaloalkyl, haloaryl, aryloxy, amino, monoalkylamino, dialkylamino, alkylamido, arylamino, arylamido. alkylthio, arylthio, heterocycloalkyl, alkylheterocycloalkyl, heterocycloalkylalkyl, heteroaryl, hetroarylalkyl, alkylheteroaryl; or $R_3$, $R_4$, or $R_7$, forms a fused cycloalkyl, heterocycloalkyl, aromatic or heteroaromatic ring with the main aromatic ring; and
$R_{10}$ is nothing, H, D, OH, halogen, oxo, nitro, CN, nitrileamido, amidosulfide, amino, aldehyde, substituted ketone, —COOH, ester, trifluoromethyl, amide, substituted or unsubstituted alkyl, alkenyl, alkynyl, aryl, arylalkyl, alkylaryl, arylsulfonyl, arylalkylenesulfonyl, alkoxy, haloalkyl, haloaryl, cycloalkyl, alkylcycloalkyl, aryloxy, monoalkylamino, dialkylamino, alkylamido, arylamino, arylamido, alkylthio, arylthio, heterocycloalkyl, alkylheterocycloalkyl, heterocycloalkylalkyl, heteroaryl, hetroarylalkyl, alkylheteroaryl; or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula IV:

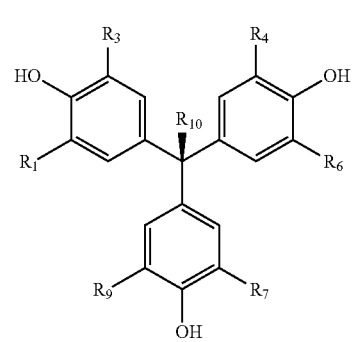

wherein $R_1$, $R_3$, $R_4$, $R_6$, $R_7$, $R_9$ and $R_{10}$ are as defined above; or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula V:

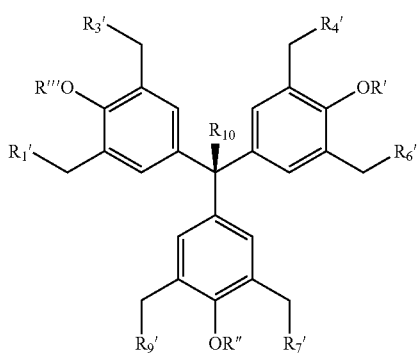

wherein
R', R", R'" are independently the same or different comprising hydrogen, alkyl, haloalkyl, phenyl, benzyl, alkanyloyl, acetyl or benzoyl;
$R_1'$, $R_3'$, $R_4'$, $R_6'$ $R_7'$, and $R_9'$ are the same or different comprising halogen, aryl, alkyl, cycloalkyl, heterocycloalkyl, alkoxy, amino, monoalkylamino, dialkylamino or arylamino group; and $R_7$ is as described above; or its isomer, pharmaceutically acceptable salt, pharmaceutical product, hydrate, N-oxide, crystal or any combination thereof, and compositions comprising the same.

In one embodiment, $R_1'$, $R_3'$, $R_4'$, $R_6'$ $R_7'$, and $R_9'$ are dialkylamino group. In another embodiment, $R_1'$, $R_3'$, $R_4'$, $R_6'$ $R_7'$, and $R_9'$ are dimethylamino group. In another embodiment, $R_1'$, $R_3'$, $R_4'$, $R_6'$ $R_7'$, and $R_9'$ are diethylamino group. In another embodiment, $R_1'$, $R_3'$, $R_4'$, $R_6'$ $R_7'$, and $R_9'$ are N-piperidine group. In another embodiment, $R_1'$, $R_3'$, $R_4'$, $R_6'$ $R_7'$, and $R_9'$ are N-pyrolidine group. In another embodiment, $R_1'$, $R_3'$, $R_4'$, $R_6'$ $R_7'$, and $R_9'$ are N-piperazine group. In another embodiment, $R_1'$, $R_3'$, $R_4'$, $R_6'$ $R_7'$, and $R_9'$ are N-piperazine-4-methyl group. In another embodiment, $R_1'$, $R_3'$, $R_4'$, $R_6'$ $R_7'$, and $R_9'$ are N-morpholine group. In another embodiment, $R_1'$, $R_3'$, $R_4'$, $R_6'$, $R_7'$, and $R_9'$ are ethoxy group.

In one embodiment, the methods of this invention comprise the use of tri-phenyl compounds represented by the structure of formula VI:

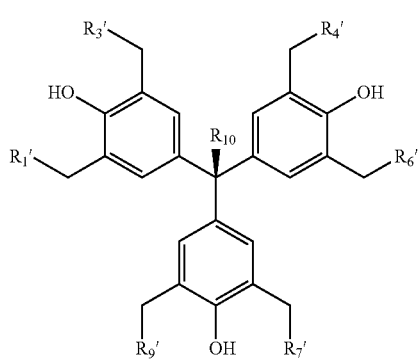

VI wherein $R_1'$, $R_3'$, $R_4'$, $R_6'$ $R_7'$, and $R_9'$ are the same or different comprising halogen, aryl, alkyl, cycloalkyl, heterocycloalkyl, alkoxy, amino, monoalkylamino, dialkylamino or arylamino group; and $R_{10}$ is as described above; or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula VII:

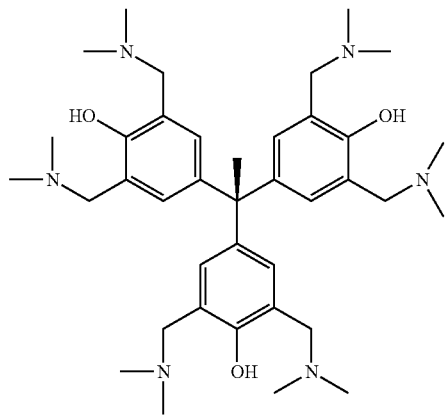

VII or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula VIII:

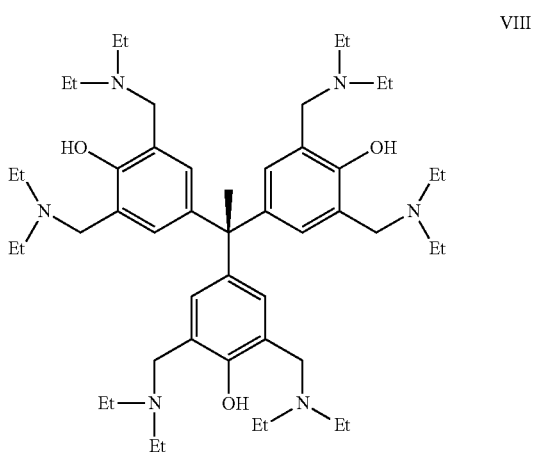

VIII or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula IX:

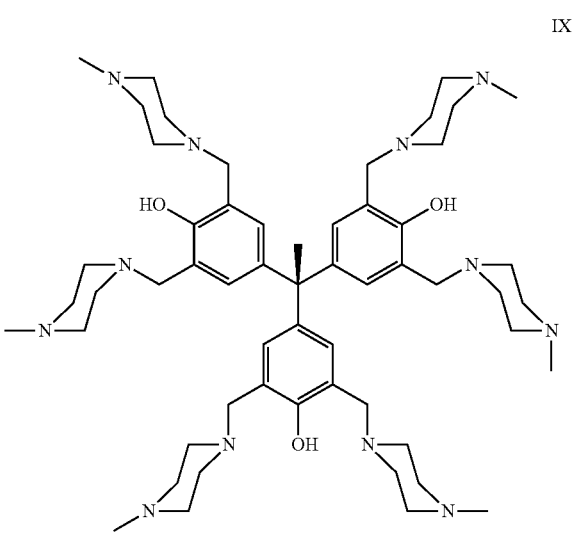

IX or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula X:

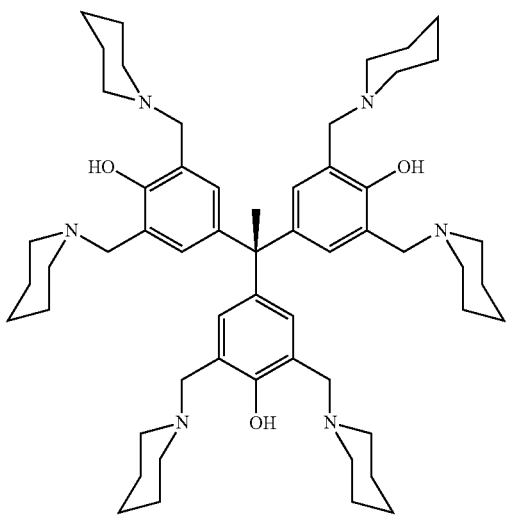

X or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula XI:

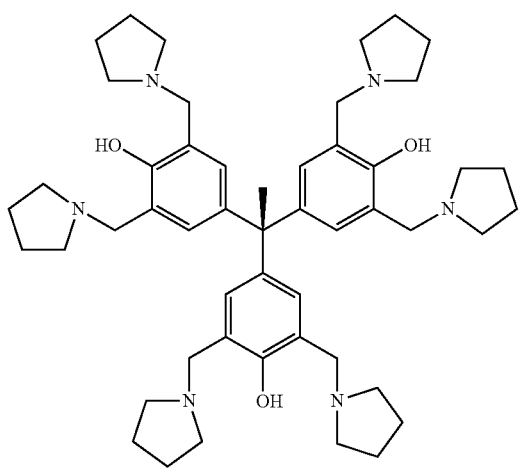

XI or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula XII:

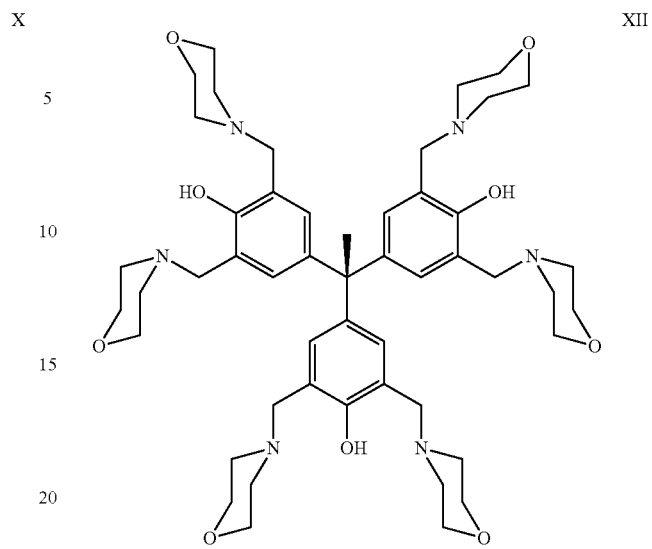

XII or its isomer, pharmaceutically acceptable salt, pharmaceutical product, hydrate, N-oxide, crystal or any combination thereof, and compositions comprising the same.

In one embodiment, the methods of this invention comprise the use of tri-phenyl compounds represented by the structure of formula XIII:

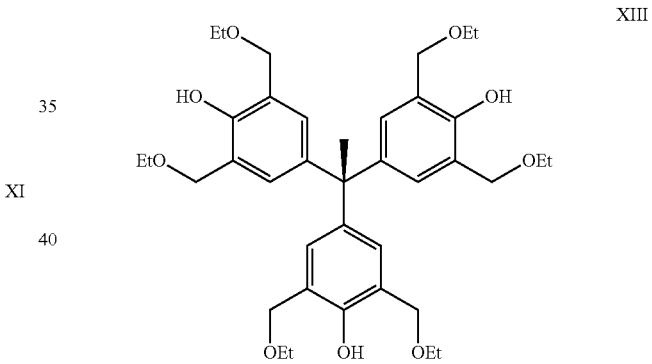

XIII or its isomer, pharmaceutically acceptable salt, pharmaceutical product, hydrate, N-oxide, crystal or any combination thereof, and compositions comprising the same.

In another embodiment the structure of formula I is represented by the structure of formula XIV:

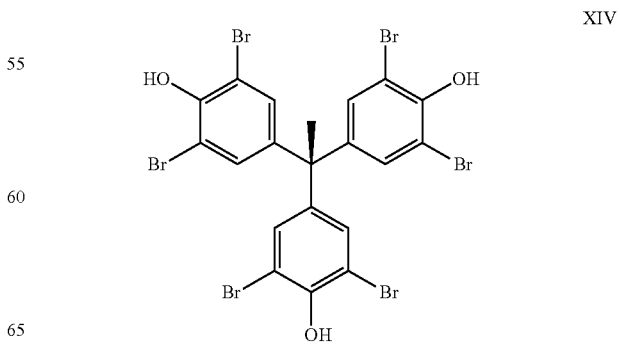

XIV or its isomer, pharmaceutically acceptable salt, pharmaceutical product, hydrate, N-oxide, crystal or any combination thereof, and compositions comprising the same.

In another embodiment the structure of formula I is represented by the structure of formula XV:

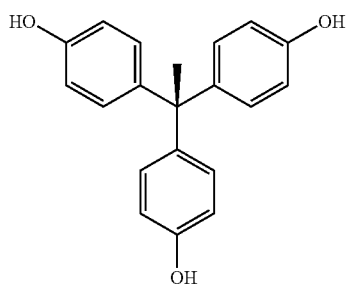

XV or its isomer, pharmaceutically acceptable salt, pharmaceutical product, hydrate, N-oxide, crystal or any combination thereof, and compositions comprising the same.

In another embodiment the structure of formula I is represented by the structure of formula XVI:

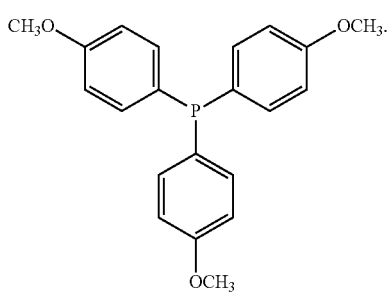

XVI or its isomer, pharmaceutically acceptable salt, pharmaceutical product, hydrate, N-oxide, crystal or any combination thereof, and compositions comprising the same.

The term "alkyl" refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-7 carbons. In another embodiment, the alkyl group has 2-6 carbons. In another embodiment, the alkyl group has 1-7 carbons. In another embodiment, the alkyl group has 2-8 carbons. In another embodiment, the alkyl group has 3-6 carbons. In another embodiment, the alkyl group has 3-7 carbons. In another embodiment, the alkyl group has 1-4 carbons. In another embodiment, the branched alkyl is an alkyl substituted by alkyl side chains of 1 to 5 carbons. In another embodiment, the branched alkyl is an alkyl substituted by haloalkyl side chains of 1 to 5 carbons. The alkyl group may be unsubstituted or substituted by a halogen, haloalkyl, hydroxyl, alkoxy, carbonyl, amido, alkylamido, dialkylamido, nitro, cyano, amino, monoalkylamino, dialkylamino, carboxyl, thio and/or thioalkyl.

An "alkenyl" group refers, in one embodiment, to an unsaturated hydrocarbon, including straight chain, branched chain and cyclic groups having one or more double bonds. The alkenyl group may have one double bond, two double bonds, three double bonds, etc. In another embodiment, the alkenyl group has 2-12 carbons. In another embodiment, the alkenyl group has 2-6 carbons. In another embodiment, the alkenyl group has 2-4 carbons. In another embodiment the alkenyl group is ethenyl ($CH=CH_2$). Examples of alkenyl groups are ethenyl, propenyl, butenyl, cyclohexenyl, etc. The alkenyl group may be unsubstituted or substituted by a halogen, hydroxy, alkoxy, carbonyl, amido, alkylamido, dialkylamido, nitro, cyano, amino, monoalkylamino, dialkylamino, carboxyl, thio and/or thioalkyl.

An alkynyl" group refers, in one embodiment, to an unsaturated hydrocarbon, including straight chain, branched chain and cyclic groups having one or more triple bonds. The alkynyl group may have one triple bond, two triple bonds, triple double bonds, etc. In another embodiment, the alkynyl group has 2-12 carbons. In another embodiment, the alkynyl group has 2-6 carbons. In another embodiment, the alkenyl group has 2-4 carbons. In another embodiment the alkynyl group is ethynyl ($-CH\equiv CH_2$). Examples of alkynyl groups are ethynyl, propynyl, butynyl, cyclohexynyl, etc. The alkynyl group may be unsubstituted or substituted by a halogen, hydroxy, alkoxy, carbonyl, amido, alkylamido, dialkylamido, nitro, cyano, amino, monoalkylamino, dialkylamino, carboxyl, thio and/or thioalkyl.

An "alkoxy" group refers, in another embodiment to an alkyl group as defined above, which is linked to oxygen. Examples of alkoxy groups are ethoxy, propoxy, tert-butoxy etc.

A "haloalkyl" group refers, in one embodiment, to an alkyl group as defined above, which is substituted by one or more halogen atoms, e.g. by F, Cl, Br or I.

An "aryl" group refers, in another embodiment, to an aromatic group having at least one carbocyclic aromatic group or heterocyclic aromatic group, which may be unsubstituted or substituted by one or more groups selected from halogen, haloalkyl, hydroxy, alkoxy, carbonyl, amido, alkylamido, dialkylamido, nitro, cyano, amino, monoalkylamino, dialkylamino, carboxy or thio or thioalkyl. In another embodiment, the aryl group is between 4-12-membered ring(s). In another embodiment, the aryl group is between 6-18-membered ring(s). In another embodiment, the aryl group is between 4-8-membered ring(s). In another embodiment, the aryl group is a 6-membered ring. In another embodiment, the aryl group is a fused ring system comprising of between 2-3 rings. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "heteroaryl" group refers, in another embodiment, to an aromatic group having at least one heterocyclic aromatic group, which may be unsubstituted or substituted by one or more groups selected from halogen, haloalkyl, hydroxy, alkoxy, carbonyl, amido, alkylamido, dialkylamido, nitro, cyano, amino, monoalkylamino, dialkylamino, carboxy or thio or thioalkyl. In another embodiment, the heteroaryl group is between 4-12-membered ring(s). In another embodiment, the heteroaryl group is between 6-18-membered ring(s). In another embodiment, the heteroaryl group is between 4-8-membered ring(s). In another embodiment, the heteroaryl group is a 6-membered ring. In another embodiment, the heteroaryl group is a fused ring system comprising of between 2-3 rings. Nonlimiting examples of heteroaryl rings are pyrrolyl, thienyl, thiazolyl, benzothienyl, naphthothienyl, purinyl, isothiazolyl, furyl, furazanyl, isobenznzofuranyl, pyranyl, chromenyl, xanthenyl, phenoxyxanthiinyl, indolyl, isoindolyl, indolizinyl, isoindolyzinyl, benzothienyl, oxazolyl, isoxazolyl, pyrazolyl, pyridyl, pyrazinyl, pyrimidinyl, pyridazinyl, and the like.

A "hydroxyl" group refers, in one embodiment, to an OH group. In some embodiments, when $R_1$, $R_2$ or $R_3$ of the compounds of the present invention is OR, then R is not OH.

In one embodiment, the term "halo" refers to a halogen, such as F, Cl, Br or I.

In another embodiment, the phrase "phenol" refers to an alcohol (OH) derivative of benzene.

An "amino" group refers to, in one embodiment, to a nitrogen atom attached by single bonds to hydrogen atoms, alkyl groups, alkenyl groups or aryl groups as described above, as described above, or a combination thereof. Non-limiting examples of amino groups are $NH_2$, $N(Me)_2$, $N(Et)_2$, $N(Ph)_2$ and the like.

A "cycloalkyl" group refers, in one embodiment, to a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, $(C_3-C_7)$cycloalkyl groups, such as cyclopropyl, cyclobutyl, cyclopentyl, cyclohexyl, and cycloheptyl, and saturated cyclic and bicyclic terpenes and $(C_3-C_7)$cycloalkenyl groups, such as cyclopropenyl, cyclobutenyl, cyclopentenyl, cyclohexenyl, and cycloheptenyl, and unsaturated cyclic and bicyclic terpenes. Preferably, the cycloalkyl group is a monocyclic ring or bicyclic to a ring structure comprising in addition to carbon atoms, sulfur, oxygen, nitrogen or any combination thereof, as part of the ring. In another embodiment the cycloalkyl is a 3-12-membered ring. In another embodiment the cycloalkyl is a 6-membered ring. In another embodiment the cycloalkyl is a 5-7-membered ring. In another embodiment the cycloalkyl is a 4-8-membered ring. In another embodiment, the cycloalkyl group may be unsubstituted or substituted by a halogen, haloalkyl, hydroxyl, alkoxy, carbonyl, amido, alkylamido, dialkylamido, cyano, nitro, $CO_2H$, amino, monoalkylamino, dialkylamino, carboxyl, thio and/or thioalkyl.

A "heterocycloalkyl" group refers, in one embodiment, to a non-aromatic, monocyclic or polycyclic ring comprising carbon and in addition to carbon, sulfur, phosphor, oxygen or nitrogen, as part of the ring. A heterocycloalkyl group can have one or more double bonds in the ring so long as the ring is not rendered aromatic by their presence. Examples of heterocycloalkyl groups include, but are not limited to, piperidine, piperazine, pyrane, morpholine. Preferably, the heterocycloalkyl group is a monocyclic ring or bicyclic to a ring structure comprising in addition to carbon atoms, sulfur, oxygen, nitrogen or any combination thereof, as part of the ring. In another embodiment the heterocycloalkyl is a 3-12-membered ring. In another embodiment the heterocycloalkyl is a 6-membered ring. In another embodiment the heterocycloalkyl is a 5-7-membered ring. In another embodiment the heterocycloalkyl is a 4-8-membered ring. In another embodiment, the heterocycloalkyl group may be unsubstituted or substituted by a halogen, haloalkyl, hydroxyl, alkoxy, carbonyl, amido, alkylamido, dialkylamido, cyano, nitro, $CO_2H$, amino, monoalkylamino, dialkylamino, carboxyl, thio and/or thioalkyl. In another embodiment the heterocycloalkyl is a cyclic urea, imidazolinyl, imidazolidinyl, pyrrolinyl, pyrrolidinyl, oxazolinyl, isoxazolinyl, oxazolidinyl, oxazolidonyl, isoxazolidonyl, pyrazolinyl, pyrazolidinyl, piperidyl, piperazine, morpholinyl.

The terms "alkylalkoxy", "alkylhaloalkyl", "alkylaryl", "alkylcycloalkyl", "alkylheterocycloalkyl", "alkylheteroaryl" and "alkylamino" refer, in one embodiment, to an alkyl group, as defined above, linked to alkoxy, haloalkyl, aryl, cycloalkyl, heterocycloalkyl, heteroaryl or amino group, respectively. The alkoxy, haloalkyl, aryl, cycloalkyl, heterocycloalkyl, heteroaryl or amino groups are as defined hereinabove. Examples include, but are not limited to, $CH_2$-OEt, $CH_2$—N-piperidine, $CH_2$—N-piperazine, $CH_2$—$N(Me)_2$, etc.

In another embodiment, the fused heterocycloalkyl of formula I-IV with the main aromatic ring forms a phenylpyrrolidone group. In another embodiment, the fused aryl of formula I-IV, with the main aromatic ring forms a naphthalene group. In another embodiment, the fused heteroaryl of formula I-IV, with the main aromatic ring forms a quinoline or isoquinoline group.

In one embodiment, this invention provides for the use of a compound as herein described and/or, its analog, derivative, isomer, metabolite, pharmaceutically acceptable salt, pharmaceutical product, hydrate, N-oxide, prodrug, polymorph, impurity or crystal or combinations thereof.

In one embodiment, the term "isomer" includes, but is not limited to, optical isomers and analogs, structural isomers and analogs, conformational isomers and analogs, and the like.

In one embodiment, the term "isomer" is meant to encompass optical isomers of the tri-phenyl compound. It is to be understood that the present invention encompasses any racemic, optically-active, polymorphic, or stereoisomeric form, or mixtures thereof, which form possesses properties useful in the treatment of telomerase expression and/or activity conditions described herein. In one embodiment, the tri-phenyl compounds are the pure (R)-isomers. In another embodiment, the tri-phenyl compounds are the pure (S)-isomers. In another embodiment, the tri-phenyl compounds are a mixture of the (R) and the (S) isomers. In another embodiment, the tri-phenyl compounds are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes "pharmaceutically acceptable salts" of the compounds of this invention, which may be produced, in one embodiment, to form alkali metal salts and to form addition salts of free acids or free bases. Suitable pharmaceutically-acceptable acid addition salts of compounds of this invention may be prepared from an inorganic acid or from an organic acid. In one embodiment, examples of inorganic acids are hydrochloric, hydrobromic, hydroiodic, nitric, carbonic, sulfuric and phosphoric acid. In one embodiment, organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, oxalic, p-toluenesulphonic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. In one embodiment, suitable pharmaceutically-acceptable base addition salts of compounds of this invention include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compounds.

Pharmaceutically acceptable salts can be prepared, from the phenolic compounds, in other embodiments, by treatment with inorganic bases, for example, sodium hydroxide. In another embodiment, esters of the phenolic compounds can be made with aliphatic and aromatic carboxylic acids, for example, acetic acid and benzoic acid esters.

The invention also includes use of N-oxides of the amino substituents of the compounds described herein.

This invention provides for the use of derivatives of the compounds as herein described. In one embodiment, "derivatives" includes but is not limited to ether derivatives, acid derivatives, amide derivatives, ester derivatives and the like. In another embodiment, this invention further includes use of hydrates of the compounds as described herein. In one embodiment, "hydrate" includes but is not limited to hemihydrate, monohydrate, dihydrate, trihydrate and the like.

The compounds of this invention may be prepared by any known method, for example, as described in U.S. patent application Ser. No. 12/602,632, or U.S. patent application Ser. No. 12/602,956, or PCT International Application Publication Number WO/2008/149346, each of which reference is hereby incorporated in its entirety.

This invention provides, in other embodiments, use of metabolites of the compounds as herein described. In one embodiment, "metabolite" means any substance produced from another substance by metabolism or a metabolic process.

This invention provides, in other embodiments, use of pharmaceutical products of the compounds as herein described. The term "pharmaceutical product" refers, in other embodiments, to a composition suitable for pharmaceutical use (pharmaceutical composition), for example, as described herein.

In some embodiments, the invention provides compositions comprising the compound of this invention or use of the compound of this invention, for treating diabetes or a disease complication arising due to diabetes.

In one embodiment, this invention provides methods of treatment using a compound of this invention, or composition comprising the same, as herein described. In some embodiments, the invention provides methods of use of a compound of this invention for the treatment of the indicated diseases, disorders or conditions, and includes use of compositions comprising the same.

In one embodiment, the terms "treating" or "treatment" includes preventive as well as disorder remittive treatment. The terms "reducing", "suppressing" and "inhibiting" have their commonly understood meaning of lessening or decreasing, in another embodiment, or delaying, in another embodiment, or reducing, in another embodiment the incidence, severity or pathogenesis of a disease, disorder or condition. In embodiment, the term treatment refers to delayed progression of, prolonged remission of, reduced incidence of, or amelioration of symptoms associated with the disease, disorder or condition. In one embodiment, the terms "treating" "reducing", "suppressing" or "inhibiting" refer to a reduction in morbidity, mortality, or a combination thereof, in association with the indicated disease, disorder or condition. In one embodiment, the term "progression" refers to an increasing in scope or severity, advancing, growing or becoming worse. The term "recurrence" means, in another embodiment, the return of a disease after a remission. In one embodiment, the methods of treatment of the invention reduce the severity of the disease, or in another embodiment, symptoms associated with the disease, or in another embodiment, reduces the number of biomarkers expressed during disease.

In one embodiment, the term "treating" and its included aspects, refers to the administration to a subject with the indicated disease, disorder or condition, or in some embodiments, to a subject predisposed to the indicated disease, disorder or condition. The term "predisposed to" is to be considered to refer, inter alia, to a genetic profile or familial relationship which is associated with a trend or statistical increase in incidence, severity, etc. of the indicated disease. In some embodiments, the term "predisposed to" is to be considered to refer, inter alia, to a lifestyle which is associated with increased risk of the indicated disease. In some embodiments, the term "predisposed to" is to be considered to refer, inter alia, to the presence of biomarkers which are associated with the indicated disease, for example, in cancer, the term "predisposed to" the cancer may comprise the presence of precancerous precursors for the indicated cancer.

In some embodiments, the term "reducing the pathogenesis" is to be understood to encompass reducing tissue damage, or organ damage associated with a particular disease, disorder or condition. In another embodiment, the term "reducing the pathogenesis" is to be understood to encompass reducing the incidence or severity of an associated disease, disorder or condition, with that in question. In another embodiment, the term "reducing the pathogenesis" is to be understood to encompass reducing the number of associated diseases, disorders or conditions with the indicated, or symptoms associated thereto.

The term "administering", in another embodiment, refers to bringing a subject in contact with a compound of the present invention. Administration can be accomplished in vitro, i.e. in a test tube, or in vivo, i.e. in cells or tissues of living organisms, for example humans. In one embodiment, the present invention encompasses administering the compounds of the present invention to a subject.

Pharmaceutical Compositions

In some embodiments, this invention provides methods of use which comprise administering a composition comprising the described compounds. As used herein, "pharmaceutical composition" means a "therapeutically effective amount" of the active ingredient, i.e. the compounds of this invention, together with a pharmaceutically acceptable carrier or diluent. A "therapeutically effective amount" as used herein refers to that amount which provides a therapeutic effect for a given condition and administration regimen.

In some embodiments, this invention provides compositions which may comprise at least one compound of this invention, in any form or embodiment as described herein. In some embodiments, the term "a" is to be understood to encompass a single or multiple of the indicated material. In some embodiments, the term "a" or "an" refers to at least one.

In some embodiments, any of the compositions of this invention will consist of a compound of this invention, in any form or embodiment as described herein. In some embodiments, of the compositions of this invention will consist essentially of a compound of this invention, in any form or embodiment as described herein.

In some embodiments, the term "comprise" refers to the inclusion of the indicated active agent, such as the compounds of this invention, as well as inclusion of other active agents, and pharmaceutically acceptable carriers, excipients, emollients, stabilizers, etc., as are known in the pharmaceutical industry. In some embodiments, any of the compositions of this invention will comprise a compound of formula I-XVI in any form or embodiment as described herein. In some embodiments, any of the compositions of this invention will consist of a compound of formula I-XVI, in any form or embodiment as described herein. In some embodiments, of the compositions of this invention will consist essentially of a compound of this invention, in any form or embodiment as described herein. In some embodiments, the term "comprise" refers to the inclusion of the indicated active agent, such as the compound of this invention, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" refers to a composition, whose only active ingredient with a comparable mode of action, or comparable molecular target is the indicated active ingredient, however, other active ingredients may be incorporated, with such secondary active ingredients acting on different targets, or in a palliative capacity. In some embodiments, the term "consisting essentially of" may refer to components which facilitate the release of the active ingredient. In some embodiments, the term "consisting" refers to a composition, which contains a compound as herein described as the only active ingredient and a pharmaceutically acceptable carrier or excipient.

In another embodiment, the invention provides a composition comprising a compound of this invention, as herein described, or its prodrug, analog, isomer, metabolite, derivative, pharmaceutically acceptable salt, pharmaceutical product, polymorph, crystal, impurity, N-oxide, ester, hydrate or any combination thereof and a suitable carrier or diluent.

An active component can be formulated into the composition as neutralized pharmaceutically acceptable salt forms. Pharmaceutically acceptable salts include the acid addition salts, which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The pharmaceutical compositions containing the compound of this invention can be administered to a subject by any method known to a person skilled in the art, such as orally, parenterally, intravascularly, paracancerally, transmucosally, transdermally, intramuscularly, intranasally, intravenously, intradermally, subcutaneously, sublingually, intraperitoneally, intraventricularly, intracranially, intravaginally, by inhalation, rectally, intratumorally, or by any means in which the recombinant virus/composition can be delivered to tissue (e.g., needle or catheter). Alternatively, topical administration may be desired for application to mucosal cells, for skin or ocular application. Another method of administration is via aspiration or aerosol formulation.

The compositions of the present invention are formulated in one embodiment for oral delivery, wherein the active compounds may be incorporated with excipients and used in the form of ingestible tablets, buccal tables, troches, capsules, elixirs, suspensions, syrups, wafers, and the like. The tablets, troches, pills, capsules and the like may also contain the following: a binder, as gum tragacanth, acacia, corn-starch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Syrup of elixir may contain the active compound, sucrose as a sweetening agent methyl, and propylparabens as preservatives, a dye and flavoring, such as cherry or orange flavor. In addition, the active compounds may be incorporated into sustained-release, pulsed release, controlled release or postponed release preparations and formulations.

In another embodiment, the compositions of this invention comprise one or more, pharmaceutically acceptable carrier materials.

In one embodiment, the carriers for use within such compositions are biocompatible, and in another embodiment, biodegradable. In other embodiments, the formulation may provide a relatively constant level of release of one active component. In other embodiments, however, a more rapid rate of release immediately upon administration may be desired. In other embodiments, release of active compounds may be event-triggered. The events triggering the release of the active compounds may be the same in one embodiment, or different in another embodiment. Events triggering the release of the active components may be exposure to moisture in one embodiment, lower pH in another embodiment, or temperature threshold in another embodiment. The formulation of such compositions is well within the level of ordinary skill in the art using known techniques. Illustrative carriers useful in this regard include microparticles of poly (lactide-co-glycolide), polyacrylate, latex, starch, cellulose, dextran and the like. Other illustrative postponed-release carriers include supramolecular biovectors, which comprise a non-liquid hydrophilic core (e.g., a cross-linked polysaccharide or oligosaccharide) and, optionally, an external layer comprising an amphiphilic compound, such as phospholipids. The amount of active compound contained in one embodiment, within a sustained release formulation depends upon the site of administration, the rate and expected duration of release and the nature of the condition to be treated suppressed or inhibited.

In one embodiment it will be desirable to deliver the compositions disclosed herein parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363, all of which are fully incorporated by reference. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. It must be stable under the conditions of manufacture and storage and must be preserved against the contaminating action of microorganisms, such as bacteria and fungi.

In another embodiment, it will be preferable to include isotonic agents, for example, sugars or sodium chloride. In other embodiments, prolonged absorption of the injectable compositions will be desirable. Prolonged absorption of the injectable compositions can be brought about by the use of agents delaying absorption, for example, aluminum monostearate and gelatin, in the compositions.

Parenteral vehicles include in certain embodiments sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like In some embodiments, the compounds of this invention may be administered at various dosages to a subject, which in one embodiment, is a human subject. In one embodiment, the compounds of this invention are administered at a dosage of 0.1-200 mg per day. In one embodiment, the compound of this invention is administered at a dose of 0.1-10 mg, or in another embodiment, 0.1-25 mg, or in another embodiment, 0.1-50 mg, or in another embodiment, 0.3-15 mg, or in another embodiment, 0.3-30 mg, or in another embodiment, 0.5-25 mg, or in another embodiment, 0.5-50 mg, or in another embodiment, 0.75-15 mg, or in another embodiment, 0.75-60 mg, or in another embodiment, 1-5 mg, or in another embodiment, 1-20 mg, or in another embodiment, 3-15 mg, or in another embodiment, 1-30 mg, or in another embodiment, 30-50 mg, or in another embodiment, 30-75 mg, or in another embodiment, 100-2000 mg. In some embodiments, the compounds of this invention may be administered at different dosages, as a function of time, or disease/symptom/condition severity, or age, or other factors, as will be appreciated by one skilled in the art.

The compounds of this invention may be administered at various dosages. In one embodiment, the compounds of this invention are administered at a dosage of 1 mg. In another embodiment the compounds of this invention are administered at a dosage of 5 mg, or in another embodiment, 3 mg, or in another embodiment 10 mg, or in another embodiment 15 mg, or in another embodiment 20 mg, or in another embodiment 25 mg, or in another embodiment 30 mg, or in another embodiment 35 mg, or in another embodiment 40 mg, or in another embodiment 45 mg, or in another embodiment 50 mg, or in another embodiment 55 mg, or in another embodiment 60 mg, or in another embodiment 65 mg, or in another embodiment 70 mg, or in another embodiment 75 mg, or in another embodiment 80 mg, or in another embodiment 85 mg, or in another embodiment 90 mg, or in another embodiment 95 mg or in another embodiment 100 mg.

While the compounds of the invention can be administered as the sole active pharmaceutical agent, they can also be used in combination with one or more other compound, and/or in combination with other agents used in the treatment and/or prevention of the diseases, disorders and/or conditions, as will be understood by one skilled in the art. In another embodiment, the compounds of the present invention can be administered sequentially with one or more such agents to provide sustained therapeutic and prophylactic effects. In another embodiment, the compounds may be administered via different routes, at different times, or a combination thereof.

In addition, the compounds of the present invention can be used, either singly or in combination, in combination with other modalities for preventing or treating conditions, diseases or disorders. In some embodiments, such other treatment modalities may include without limitation, surgery, radiation, hormone supplementation, diet regulation, wound debridement, etc., as will be appropriate for the condition being treated. These can be performed sequentially (e.g., treatment with a compound of the invention following surgery or radiation) or in combination (e.g., in addition to a diet regimen).

The additional active agents may generally be employed in therapeutic amounts as indicated in the PHYSICIANS' DESK REFERENCE (PDR) 53rd Edition (1999), or such therapeutically useful amounts as would be known to one of ordinary skill in the art. The compounds of the invention and the other therapeutically active agents can be administered at the recommended maximum clinical dosage or at lower doses. Dosage levels of the active compounds in the compositions of the invention may be varied to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

The pharmaceutical composition can comprise the compounds of this invention alone or can further include a pharmaceutically acceptable carrier and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulose materials, and mixtures thereof. The pharmaceutical preparation containing the compounds of this invention can be administered to a subject by, for example, subcutaneous implantation of a pellet; in a further embodiment, the pellet provides for controlled release of the compounds of this invention over a period of time. The preparation can also be administered by intravenous, intraarterial, or intramuscular injection of a liquid preparation, oral administration of a liquid or solid preparation, or by topical application. Administration can also be accomplished by use of a rectal suppository or a urethral suppository. The pharmaceutical composition can also be a parenteral formulation; in one embodiment, the formulation comprises a liposome that includes a complex of a compound of this invention.

The pharmaceutical composition of the invention can be prepared by known dissolving, mixing, granulating, or tablet-forming processes. For oral administration, the compounds of this invention or their physiologically tolerated derivatives such as salts, esters, N-oxides, and the like are mixed with additives customary for this purpose, such as vehicles, stabilizers, or inert diluents, and converted by customary methods into a suitable form for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders like acacia, cornstarch, gelatin, or with disintegrating agents such as cornstarch, potato starch, alginic acid, or with a lubricant such as stearic acid or magnesium stearate. Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the compounds of this invention or their physiologically tolerated derivatives such as salts, esters, N-oxides, and the like are converted into a solution, suspension, or emulsion, if desired with the substances customary and suitable for this purpose, for example, solubilizers or other auxiliaries. Examples are: sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Typically, such compositions are prepared as an aerosol of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, or pH buffering agents which enhance the effectiveness of the active ingredient.

For topical administration to body surfaces using, for example, creams, gels, drops, and the like, the compounds of this invention or their physiologically tolerated derivatives such as salts, esters, N-oxides, and the like are prepared and applied as solutions, suspensions, or emulsions in a physiologically acceptable diluent with or without a pharmaceutical carrier.

In another embodiment, the active compound can be delivered in a vesicle, in particular a liposome (see Langer, Science 249:1527-1533 (1990); Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 317-327; see generally ibid).

In one embodiment, the present invention provides combined preparations. In one embodiment, the term "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

It is to be understood that this invention is directed to compositions and combined therapies as described herein, for any disease, disorder or condition, as appropriate, as will be appreciated by one skilled in the art. Certain applications of such compositions and combined therapies have been described hereinabove, for specific diseases, disorders and conditions, representing embodiments of this invention, and methods of treating such diseases, disorders and conditions in a subject by administering a compound as herein described, alone or as part of the combined therapy or using the compositions of this invention represent additional embodiments of this invention.

Treatment of Diabetes and Disease Complications Arising from Same

Telomere shortening has been found to occur in some diabetes patient samples, which in turn may be attributable to pancreatic beta islet cell death, a phenomenon observed in diabetes. Telomerase has been suggested to possess anti-apoptotic activity and has been suggested to act as a cellular protector from oxidative stress and damage. Telomerase expression in adult cells, however, is reported to be minimal, at best, in healthy tissue.

The Compounds of Formula I can activate or enhance telomerase expression or activity.

This invention provides a method of reducing circulating glucose levels, reducing insulin resistance, stimulating or increasing insulin sensitivity, stimulating or increasing pancreatic beta-cell mass, or stimulating or increasing creatinine clearance in a subject in need thereof, or preventing or reducing renal damage in a diabetic subject in need thereof, said method comprising administering to a subject a compound represented by the structure of formula I, which in some embodiments, includes selection of a specific subset of the compounds encompassed by formula I.

In some embodiments, this subset of compounds, in addition to interacting with the telomerase enzyme and stimulating and/or increasing telomerase expression and/or activity in the tissues and cells of the subject is superiorly capable of reducing circulating glucose levels, reducing insulin resistance, stimulating or increasing insulin sensitivity, stimulating or increasing pancreatic beta-cell mass, or stimulating or increasing creatinine clearance in a subject in need thereof, or preventing or reducing renal damage in a diabetic subject.

In particular, in some aspects the compounds for use in the methods of this invention consist essentially of

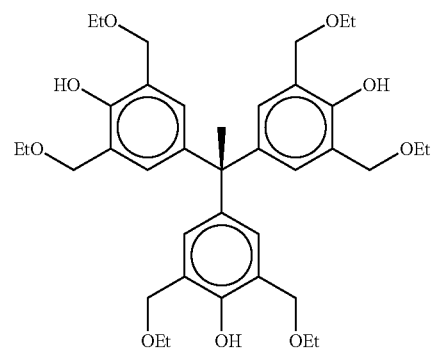

1,1,1,1-tris (4-hydroxy-3, 5-methylene ethoxy-phenyl)-ethane or

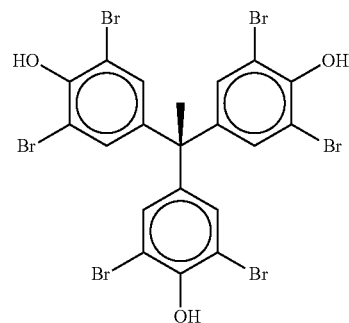

1,1,1-tris (4-hydroxy-3, 5-dibromo-phenyl)-ethane

In some embodiments, the compounds for use in the methods of this invention consist essentially of a compound of formula:

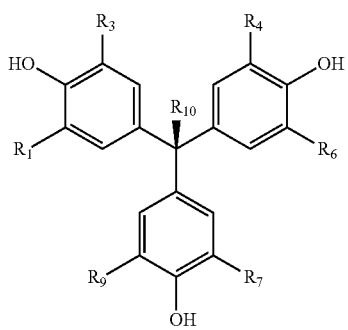

wherein

R$_1$, R$_3$, R$_4$, R$_6$, R$_7$ and R$_9$ are the same or different, halogen, CN, nitrileamido, trifluoromethyl, substituted alkyl, alkoxy, alkylalkoxy, haloalkyl, alkylhaloalkyl, and R$_{10}$ is nothing, H, D, OH, halogen, oxo, substituted or unsubstituted alkyl, alkoxy, haloalkyl, or its isomer, pharmaceutically acceptable salt, pharmaceutical product, hydrate, N-oxide, polymorph, crystal or any combination thereof.

As exemplified herein, use of a compound of formula I, and in particular, a compound of formula II, and in particular, a compound of formula XI, XIII and XIV promoted reduction of circulating glucose levels in diabetic animals, increase of pancreatic beta cell mass, and reduced kidney damage in diabetic subjects.

In another embodiment, the invention provides for the methods as herein described, wherein said subject is administered a second agent, which is useful in the treatment of diabetes or diabetes related complications. According to this aspect, and in some embodiments, the subject is administered a second agent, which is useful in the reduction of circulating glucose levels, reduction of insulin resistance, stimulation or increase of insulin sensitivity, stimulation or increase of pancreatic beta-cell mass, or stimulation or increase of creatinine clearance in a subject, or prevention or reduction of renal disease in said subject.

Non-limiting examples of other active compounds which are used in the treatment of diabetes mellitus type 2 and/or type 1 are provided in the following list:

Insulin and insulin analogues
Glucagon-Like-Peptide-1 (GLP-1) receptor agonists
Sulfonylurea agents
Biguanide agents
Alpha-glucosidase inhibitors
PPAR-Agonists
Meglitinide agents
Dipeptidyl-peptidase (DPP) IV inhibitors
PDE1, PDE5, PDE9, PDE10 or PDE11 inhibitors
Amylin agonists
Cinnamon
Glucagon receptor antagonists
Glycogen-Phosphorylase inhibitors
Fructose-1,6-Bisphosphate inhibitors
Cannabinoid (CB1) receptor antagonists
Anti-obesity drugs such as appetite suppressors, satiety increasing substances, and energy expenditure increasing drugs and pharmaceutically acceptable salts thereof.

In another embodiment of the present invention the other active compound which is used in the treatment of diabetes mellitus type 2 and/or type 1 is insulin. Specific examples of insulin include, but are not limited to Humulin® [human insulin, (rDNA origin)], Novolin® [human insulin, (rDNA origin)], Velosulin® BR [human buffered regular insulin, (rDNA origin)] and Exubera® [human insulin, inhaled].

In another embodiment of the present invention the other active compound which is used in the treatment of diabetes mellitus type 2 and/or type 1 is an insulin analogue or a pharmaceutically acceptable salt thereof. Specific examples of insulin analogues include, but are not limited to, novarapid, insulin detemir, insulin lispro, insulin glargine, insulin zinc suspension and Lys-Pro insulin.

In another embodiment of the present invention the other active compound which is used in the treatment of diabetes mellitus type 2 and/or type 1 is a Glucagon-Like-Peptide-1 receptor agonist or a pharmaceutically acceptable salt thereof. Specific examples of Glucagon-Like-Peptide-1 receptor agonists include, but are not limited to BIM-51077 (CAS-No. 275371-94-3), EXENATIDE (CAS-No. 141758-74-9), LIRAGLUTIDE (CAS-No. 20656-20-2), ALBIGLUTIDE (CAS-No. 782500-75-8) and ZP-10 (CAS-No. 320367-13-3). A preferred Glucagon-Like-Peptide-1 receptor agonist is EXENATIDE.

In another embodiment of the present invention the other active compound which is used in the treatment of diabetes mellitus type 2 and/or type 1 is a sulfonylurea agent or a pharmaceutically acceptable salt thereof. Specific examples of sulfonylurea agents include, but are not limited to, TOLBUTAMIDE (CAS-No. 000064-77-7), TOLAZAMIDE (CAS-No. 001156-19-0), GLIPIZIDE (CAS-No. 029094-61-9), CARBUTAMIDE (CAS-No. 000339-43-5), GLISOXEPIDE (CAS-No. 025046-79-1), GLISENTIDE (CAS-No. 032797-92-5), GLIBORNURIDE (CAS-No. 026944-48-9), GLIBENCLAMIDE (CAS-NO. 010238-21-8), GLIQUIDONE (CAS-No. 033342-05-1), GLIMEPIRIDE (CAS-No. 093479-97-1) and GLICLAZIDE (CAS-No. 021187-98-4).

In another embodiment of the present invention the pharmaceutically acceptable salt of TOLBUTAMIDE is the sodium salt of TOLBUTAMIDE. In another embodiment of the present invention the pharmaceutically acceptable salt of GLIQUIDONE is the sodium salt of GLIQUIDONE.

In another embodiment of the present invention the other active compound which is used in the treatment of diabetes mellitus type 2 and/or type 1 is a biguanide agent or a pharmaceutically acceptable salt thereof. A specific example of a biguanide agent includes, but is not limited to METFORMIN (CAS-No. 000657-24-9).

In another embodiment of the present invention the pharmaceutically acceptable salt of METFORMIN is the hydrochloride salt of METFORMIN.

In another embodiment of the present invention the other active compound which is used in the treatment of diabetes mellitus type 2 and/or type 1 is an alpha-glucosidase-inhibitor or a pharmaceutically acceptable salt thereof. Specific examples of alpha-glucosidase-inhibitors include, but are not limited to ACARBOSE (Cas-No. 056180-94-0), MIGLITOL (CAS-No. 072432-03-2) and VOGLIBOSE (CAS-No. 083480-29-9).

In another embodiment of the present invention the other active compound which is used in the treatment of diabetes mellitus type 2 and/or type 1 is a PPAR-agonist or a pharmaceutically acceptable salt thereof. Specific examples of PPAR-agonists include, but are not limited to MURAGLITAZAR (CAS-No. 331741-94-7), ROSIGLITAZONE (CAS-NO. 122320-73-4), PIOGLITAZONE (CAS-No. 111025-46-8), FARGLITAZAR (CAS-No. 196808-45-4), NAVEGLITAZAR (CAS-No. 476436-68-7), NETOGLITAZONE (CAS-NO. 161600-01-7), RIVOGLITAZONE (CAS-No. 185428-18-6), K-111 (CAS-No. 221564-97-2), SODELGLITAZAR (=GW-677954; CAS-No. 622402-24-8) and (−)-Halofenate (CAS-No. 024136-23-0). Preferred PPAR-agonists are ROSGLITAZONE and PIOGLITAZONE.

In another embodiment of the present invention the pharmaceutically acceptable salt of ROSIGLITAZONE is the maleate salt of ROSIGLITAZONE. In another embodiment of the present invention the pharmaceutically acceptable salt of RIVOGLITAZONE is the hydrochloride salt of RIVOGLITAZONE. In another embodiment of the present invention the pharmaceutically acceptable salt of K-111 is the sodium salt of K-111. In another embodiment of the present invention the pharmaceutically acceptable salt of PIOGLITAZONE is the dihydrochloride salt of PIOGLITAZONE.

In another embodiment of the present invention the other active compound which is used in the treatment of diabetes mellitus type 2 and/or type 1 is a meglitinide agent or a pharmaceutically acceptable salt thereof. Specific examples of meglitinide agents include, but are not limited to REPAGLINIDE (CAS-No. 135062-02-1), NATEGLINIDE (CAS-No. 105816-04-4) and MITIGLINIDE (CAS-No. 145375-43-5).

In another embodiment of the present invention the pharmaceutically acceptable salts of MITIGLINIDE are the monopotassium or the calcium salt of MITIGLINIDE.

In another embodiment of the present invention the other active compound which is used in the treatment of diabetes mellitus type 2 and/or type 1 is a DPP-IV inhibitor or a pharmaceutically acceptable salt thereof. Specific examples of DPP IV inhibitors include, but are not limited to SITAGLIPTIN (CAS-No. 486460-32-6), SAXAGLIPTIN (CAS-No. 361442-04-8), VILDAGLIPTIN (CAS-No. 274901-16-5), DENAGLIPTIN (CAS-No. 483369-58-0), ALOGLIPTIN (CAS-No. 850649-61-5) and P32/98 (CAS-No. 251572-70-0).

In another embodiment of the present invention the pharmaceutically acceptable salt of SITAGLIPTIN is the phosphate salt of SITAGLIPTIN. In another embodiment of the present invention the pharmaceutically acceptable salt of ALOGLIPTIN is the benzoate salt of ALOGLIPTIN. In another embodiment of the present invention the pharmaceutically acceptable salts of P32/98 are the fumarate or hydrochloride salt of P32/98.

In another embodiment of the present invention the other active compound which is used in the treatment of diabetes mellitus type 2 and/or type 1 is a PDE5 inhibitor or a pharmaceutically acceptable salt thereof. Specific examples of PDE5 inhibitors include, but are not limited to SILDENAFIL (CAS-No. 139755-83-2), VARDENAFIL (CAS-No. 224785-90-4), TADALAFIL (CAS-No. 171596-29-5), UDENAFIL (CAS-No. 268203-93-6) and AVANAFIL (CAS-No. 330784-47-9).

In another embodiment of the present invention the pharmaceutically acceptable salts of SILDENAFIL are the hemicitrate, the citrate or the mesilate salt of SILDENAFIL; particularly preferred is the citrate salt of SILDENAFIL. In another embodiment of the present invention the pharmaceutically acceptable salts of VARDENAFIL are the monohydrochloride salt of VARDENAFIL or the dihydrochloride salt of VARDENAFIL. In another embodiment of the present invention the pharmaceutically acceptable salt of AVANAFIL is the besilate salt of AVANAFIL.

In another embodiment of the present invention the other active compound which is used in the treatment of diabetes mellitus type 2 and/or type 1 is a PDE1, PDE9, PDE10 or PDE11 inhibitor or a pharmaceutically acceptable salt thereof. PDE1, PDE9, PDE10 or PDE11 inhibitors which may be useful employed according to the present invention, can be found, for example, in
US20020160939,
WO03037432,
US2004220186,
WO2005003129,
WO2005012485,
WO2005120514 and
WO03077949.

In another embodiment of the present invention the other active compound which is used in the treatment of diabetes mellitus type 2 and/or type 1 is an amylin agonist or a pharmaceutically acceptable salt thereof. A specific example of an amylin agonist includes, but is not limited to PRAMLINITIDE (CAS-No. 151126-32-8).

In another embodiment of the present invention the pharmaceutically acceptable salt of PRAMLINITIDE is the acetate salt of PRAMLINITIDE.

In another embodiment of the present invention the other active compound which is used in the treatment of diabetes mellitus type 2 and/or type 1 is cinnamon.

In another embodiment of the present invention the other active compound which is used in the treatment of diabetes mellitus type 2 and/or type 1 is a glucagon receptor antagonist or a pharmaceutically acceptable salt thereof. A specific example of a glucagons receptor antagonist includes, but is not limited to BAY-27-9955 (CAS-No. 202855-56-9).

In another embodiment of the present invention the other active compound which is used in the treatment of diabetes mellitus type 2 and/or type 1 is a glycogen-phosphorylase inhibitor or a pharmaceutically acceptable salt thereof. An example of a glycogen-phosphorylase inhibitor includes, but is not limited to INGLIFORIB (CAS-No. 186392-65-4).

In another embodiment of the present invention the other active compound which is used in the treatment of diabetes mellitus type 2 and/or type 1 is a fructose-1,6-bisphosphate inhibitor or a pharmaceutically acceptable salt thereof. An example of a fructose-1,6-bisphosphate inhibitor includes, but is not limited to MANAGLINAT DIALANETIL (=MB-06322; CAS-No. 280782-97-0) and MB-05032 (Cas-No. 261365-11-1).

In another embodiment of the present invention the pharmaceutically acceptable salt of MB-05032 is the hydrobromide salt of MB-05032.

In another embodiment of the present invention the other active compound which is used in the treatment of diabetes mellitus type 2 and/or type 1 is a cannabinoid (CB1) receptor antagonist or a pharmaceutically acceptable salt thereof. Specific examples of cannabinoid (CB1) receptor antagonists include, but are not limited to AVE-1625 (CAS-No. 261922-46-7), RIMONABANT (CAS-No. 168273-06-1) and SURINABANT (CAS-No. 288104-79-0).

In another embodiment of the present invention the pharmaceutically acceptable salt of RIMONABANT is the hydrochloride salt of RIMONABANT.

In another embodiment of the present invention the other active compound which is used in the treatment of diabetes mellitus type 2 and/or type 1 is an anti-obesity drug or a pharmaceutically acceptable salt thereof. Specific examples of anti-obesity drugs include, but are not limited to HMR-1426 (CAS-No. 262376-75-0), CETILISTAT (CAS-No. 282526-98-1) and SIBUTRAMINE (CAS-No. 106650-56-0).

In another embodiment of the present invention the pharmaceutically acceptable salt of HMR-1426 is the hydrochloride salt of HMR-1426. In another embodiment of the present invention the pharmaceutically acceptable salt of SIBUTRAMINE is the hydrochloride salt of SIBUTRAMINE.

Additional information with regard to the preparation, suitable dosage forms and dose ranges of the glucagon-like-peptide-1 receptor agonists listed in Table 1 can be found in the following patents/patent applications:
WO0334331,
EP0981611,
WO9808871,
WO0104156, and
WO03059934.

The sulfonylurea agents TOLBUTAMIDE, TOLAZAMIDE, GLIPIZIDE, CARBUTAMIDE, GLISOXEPIDE; GLISENTIDE, GLIBORNURIDE, GLIBENCLAMIDE, GLIQUIDONE, GLIMEPIRIDE and GLICLAZIDE are commercially available. The person skilled in the art is familiar with suitable formulations and dose ranges of these compounds.

The biguanide agent METFORMIN is commercially available. The person skilled in the art is familiar with suitable formulations and dose ranges of this compound.

The alpha-glucosidase inhibitors ACARBOSE, MIGLITOL and VOGLIBOSE listed in Table 1 are commercially available. The person skilled in the art is familiar with suitable formulations and dose ranges of this compound.

Additional information with regard to the preparation, suitable dosage forms and dose ranges of the PPAR-agonists can be found in the following patents/patent applications:
WO0121602,
EP03306228,
EP0658161,
EP0193256,
WO9731907,
WO0140169,
WO02100813,
EP0604983,
EP0745600,
WO9615784,
WO0259098, and
EP1183020.

The metiglinide agents REPAGLINIDE, NATEGLINIDE and MITIGLINIDE are commercially available. The person skilled in the art is familiar with suitable formulations and dose ranges of this compound.

Additional information with regard to the preparation, suitable dosage forms and dose ranges of the DPP IV inhibitors can be found in the following patents/patent applications:
WO03004498,
WO0168603,
WO0034241,
WO0302531,
WO9961431, and
WO2005095381.

Additional information with regard to the preparation, suitable dosage forms and dose ranges of the PDE5 inhibitors can be found in the following patents/patent applications:
WO0213798,
WO0260422,
WO2004082667,
WO0027848, and
EP1219609.

Additional information with regard to the preparation, suitable dosage forms and dose ranges of the amylin analogue PRAMLINTIDE listed in Table 1 can be found in EP0567626.

Additional information with regard to the preparation, suitable dosage forms and dose ranges of the glucagon receptor antagonist can be found in WO09804528.

Additional information with regard to the preparation, suitable dosage forms and dose ranges of the glycogen-phosphorylase inhibitor can be found in WO9639385.

Additional information with regard to the preparation, suitable dosage forms and dose ranges of the fructose-1,6-bisphosphate inhibitors can be found in
WO0001495 and
WO0147935.

Additional information with regard to the preparation, suitable dosage forms and dose ranges of the cannabinoid (CB1) receptor antagonist can be found in
EP1112251,
EP0576357 and
WO0046209.

Additional information with regard to the preparation, suitable dosage forms and dose ranges of HMR-1426, CETILISTAT and SIBUTRAMINE can be found in the following patents/patent applications:
WO0018749,
EP1144395 and
EP0397831.

"Pharmaceutically acceptable salts" of Compound A or the other active compound(s) which is (are) used in the treatment of diabetes mellitus type 2 and/or type 1 are not limited to the specific examples given above. The term refers to non-toxic salts of these compounds. These pharmaceutically acceptable salts are generally prepared by reacting a free base with a suitable organic or inorganic acid or by reacting an acid with a suitable organic or inorganic base. Particular mention may be made of the pharmaceutically acceptable inorganic and organic acids customarily used in pharmacy. Those suitable are in particular water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 1-hydroxy-2-naphthoic acid. As examples of pharmaceutically acceptable salts with bases may be mentioned the lithium, sodium, potassium, calcium, aluminium, magnesium, titanium, ammonium, meglumine or guanidinium salts.

In another embodiment, the invention provides for the use of a compound as described herein or a pharmaceutical composition comprising compounds as described herein for the preparation of a medicament for use in reducing circulating glucose levels, reducing insulin resistance, stimulating or increasing insulin sensitivity, stimulating or increasing pancreatic beta-cell mass, or stimulating or increasing creatinine clearance in a subject in need thereof, or preventing or reducing renal damage in a diabetic subject in need thereof. In some embodiments, the medicament may further comprise a second agent, which is useful in the treatment of diabetes or diabetes related complications. In some embodiments, the use may include such use by a subject who is diabetic, and receiving therapy with an alternate agent, which is useful in the treatment of diabetes or diabetes related complications.

The following examples are presented in order to more fully illustrate the preferred embodiments of the invention. They should in no way be construed, however, as limiting the broad scope of the invention.

EXAMPLES

Example 1

Compounds of this Invention Reduce Blood Glucose Levels after Fast

The effect of compounds of the present invention on diabetes per se, and disease complications arising as a result of diabetes was evaluated. Streptozotocin treatment of mice and rats are known in vivo diabetes models. Intraperitoneal injections of reduced STZ concentrations (35 mg/kg) was evaluated in mice and rats, in order to determine whether in a model causing only partial damage to pancreatic islet β-cells, whether the compounds of this invention would be helpful.

Treatment with Compound AGS-500 was evaluated in this context.

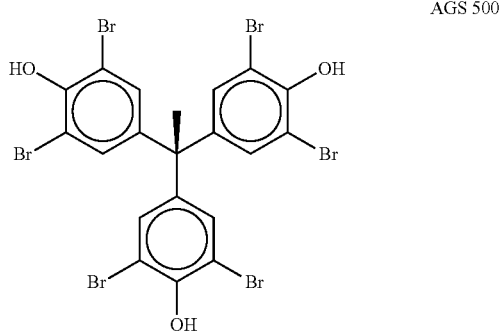

AGS 500

1,1,1-tris (4-hydroxy-3, 5-dibromo-phenyl)-ethane

Any of the compounds referred to herein for use, in the Examples and Description contained herein, may be prepared by any known method, for example, as described in U.S. patent application Ser. No. 12/602,632, or U.S. patent application Ser. No. 12/602,956, or PCT International Application Publication Number WO/2008/149346, each of which reference is hereby incorporated in its entirety.

Eight-week-old Wistar female rats received two doses of STZ administered intraperitoneally (60 or 35 mg/kg in 0.1M Citrate buffer; at 5-day intervals), which induced diabetes in all animal, since not all rats that received a single injection of STZ became diabetic in this model. These animals were then treated every 3 days with a subcutaneous injection of compound AGS-500 (6 mg/kg) for from 2-5 weeks to generate a Type I Diabetes phenotype.

Blood glucose levels were monitored every 3 days in the rats. Ten weeks after the beginning of this study, each mice group was divided into 2 sub-groups, one of each also received insulin (4 U\Kg) every 2 days, except for the non-diabetic sub-groups. Acetic acid (1%) served as the vehicle control. Diabetes was diagnosed when non-fasting blood glucose levels were above 200 mg/dl.

Glucose Tolerance Test: Animals were fasted for 12 hr with free access to water. Blood-glucose levels after fast were measured and then the animals received an i.p. injection of glucose (1.5 g/kg). Blood samples were taken at several intervals (for the duration of 2 hr), when glucose levels above 200 mg/dl at 2 hr confirmed a diagnosis of diabetes.

Creatinine Clearance and Urine Total Protein Level: Animals were housed in metabolic cages, one animal per cage, for 24 hours in order to collect urine. Urine creatinine values were assessed to calculate Creatinine Clearance (CrCl) as an indicator of Glomerular Filtration Rate (GFR) using the Standard Jaffe Reaction. Urine total protein level was examined using the Microprotein-PR method. Body weight was also measured, on average, every 3 days.

AGS-500 treatment of Rats as described had no effect on the rat hyperglycemic state. Blood glucose levels in treated animals was comparable in AGS-500 administered groups, as compared to controls (Citrate: 79.5±1.5 mg/dl; STZ: 289±7 mg/dl; STZ+DMSO: 333±21 mg/dl; STZ+AGS-500: 275±18 mg/dl).

Extension of these studies included treatment of rats divided into 4 groups, as follows: 3 groups received 2 injections of STZ (35 mg/kg) at day 0' and day 15', serving as the diabetic group, while the non-diabetic group received 2 injections of Citrate buffer in accordance with the stated schedule. One diabetic group was administered AGS-500 intraperitoneally (6 mg/kg) every 12 hours (12 h) starting at day 4', the second diabetic group received DMSO every 12 h starting at day 4', and a third diabetic group was not injected with either AGS-500 or DMSO.

No reduction in blood glucose levels of non-fasting animals, which were measured throughout the experiment, was observed in any of the diabetic groups (FIG. 1A). A significant reduction of blood glucose levels to normal was seen when fasting glucose levels were assessed (following 12 h fast), only in the diabetic group administered AGS-500 every 12 h (FIG. 1B). [0182]7 week-old female ICR mice were intra-peritoneally injected with STZ (40 mg\Kg) for 5 consecutive days. Non-diabetic mice received citrate buffer (pH 4.3, cold), which served as the vehicle controls for this study. AGS-500 (6 mg\Kg) was then administered subcutaneously every 2 days, for 5 months, on the first day after STZ administration. A further control group, where DMSO was administered in accordance with this regimen, was included. Mice were divided into the following 6 groups (10 mice per group except STZ only-5 mice):

STZ only
STZ+DMSO
Citrate+DMSO 1% every day
STZ+AGS-499 (6 mg/kg) injected every day S.C
STZ+AGS-500 (6 mg/kg) injected every day S.C
STZ+AGS-500 (6 mg/kg) injected every other day S.C Mice were weighed and blood glucose levels were measured using a free style glucometer. Food consumption was also measured 24 hours prior to STZ injection. The concentration of STZ to be injected was calculated. STZ at 40 mg/kg was injected ip for 5 consecutive days. AGS treatment was administered one day following the last STZ injection.

The establishment of diabetes was validated by the assessment of blood glucose levels performed every 3 days (at the beginning) and once a week after 59 days from the initiation of the experiment. Blood glucose levels over 200 mg/dl (measured 3 consecutive times) indicated a diabetic state.

Mice were weighed every 3 days and dosages were adjusted, as appropriate, in view of the obtained weight values. At 36 days, 77 days and 126 days after the onset of diabetes, food consumption measurement was performed.

A Glucose Tolerance Test (GTT) was performed at 2.5 months and 5 months from the initiation of the experiment.

Mice were subjected to 12 hours fast (with water) weighed, blood glucose level was measured and Glucose at 1.5 gr/kg in no more than 100 μl was injected IP. Blood glucose levels were measured at 10, 20, 30, 60, 90 and 120 min after glucose injection. glucose tolerance test.

Urine was collected and urine volume was measured. Urine ketone levels were estimated. Urine glucose level was measured, urine pH, urine bilirubin, the presence of blood, leukocytes, urobilinogen, and nitrite and urine specific gravity were measured. Analysis of the data is now inprogress.

At 80 days from the initiation of the experiments each group was divided to 2 subgroups which received either insulin (4 units/kg) or acetic acid (0.015%) both in HEPES buffer (pH 7.45) injected every 48 hours. Mice were sacrificed after 5 months from the initiation of the experiments.

Blood glucose levels were monitored every 3 days. Ten weeks after the beginning of this study, each group was divided into 2 sub-groups, one of each also received insulin (4 U\Kg) every 2 days, except for the non-diabetic subgroups. Acetic acid (1%) served as the vehicle control.

The compounds AGS 499 and 500 were administered after the 5th STZ injection, i.e. after the destruction of most of the beta cells in the pancreas. An increase in blood glucose levels over time was observed in all treatment groups, however AGS compound treatment plateued, while glucose levels continued to rise in control groups (FIG. 2A). Treatment with AGS 500 every 48 hrs. exhibited the best effect in reducing blood glucose levels with time. Blood glucose levels ten weeks after the first AGS-500 injection, a group of mice receiving insulin (4 U\Kg) every 2 days versus controls, as well (FIG. 2B-E). As expected, insulin lowered circulating glucose levels in control groups (FIG. 2C, separating out insulin treatment of STZ-induced diabetic mice as the sole treatment group).

Figure 2E:
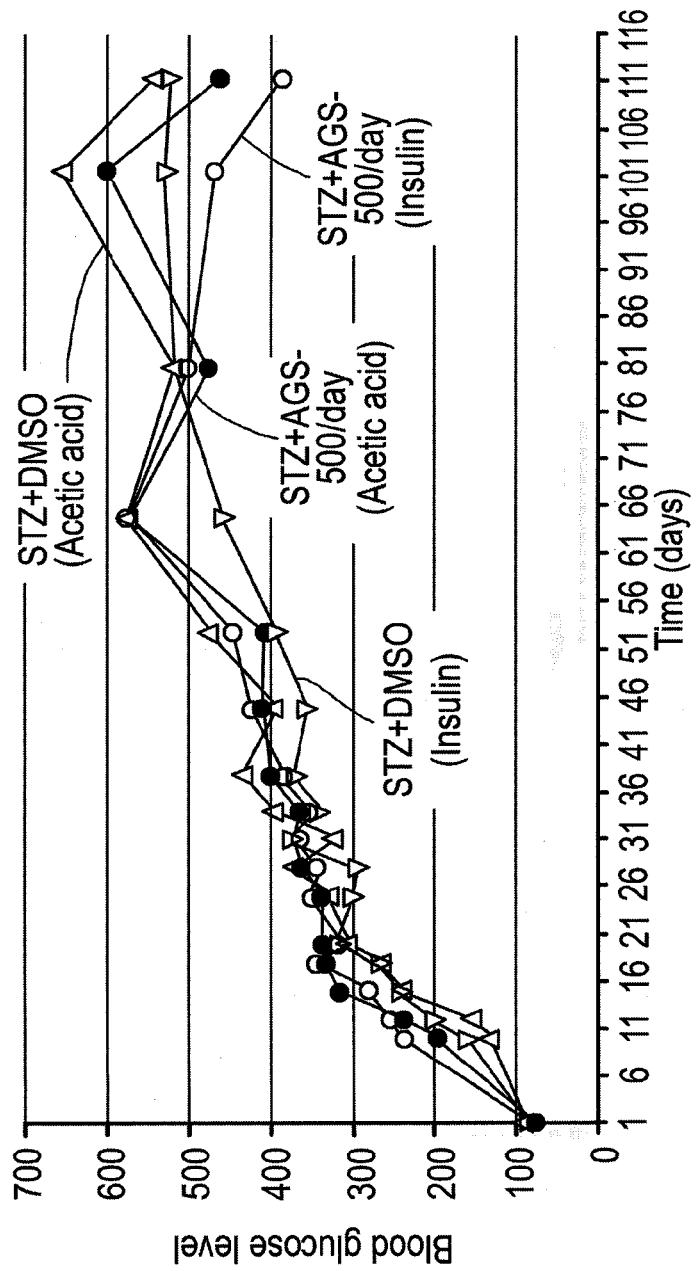

Combined AGS-499 and insulin treatment reduced blood glucose levels over time by more than 20% as compared to insulin treatment alone (FIG. 2D). Combined AGS-500 and insulin treatment, as well, reduced blood glucose levels over time by more than 20% as compared to insulin treatment alone (FIG. 2E). While indeed the combined AGS-500 and insulin treatment reduced circulating glucose levels in STZ treated animals, AGS-500 treatment alone showed the greatest therapeutic effect (FIG. 2F).

Figures 1, 2G:
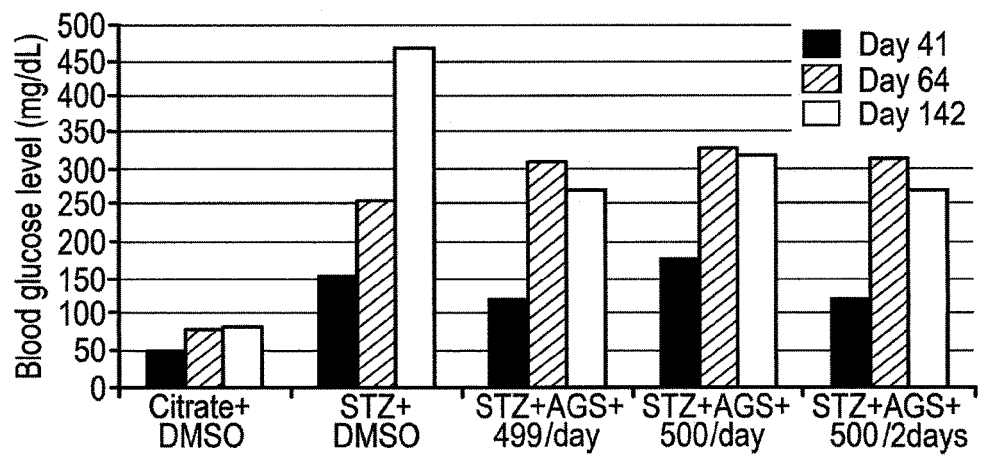
FIG. 2G-1 and FIG. 2G-2 shows fasting circulating glucose levels in subjects following treatment with the indicated regimens, in the presence or absence of insulin.

When fasting glucose levels were assessed, it was found that treatment with AGS compounds reduced (by 20%) circulating glucose levels, however, combined AGS-compound and insuling therapy did not exhibit an additive effect in reducing such levels (FIG. 2G, p≤0.05, n≥4).

Figure 3A:
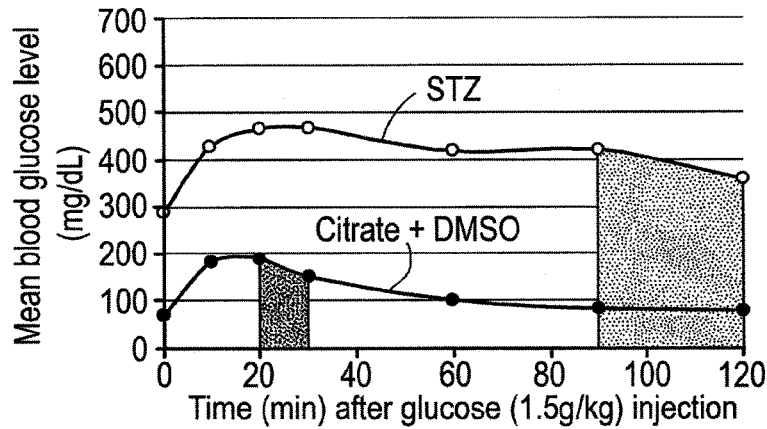
FIGS. 3A-3E: Result of GTT test performed after 2 months showing the mean circulating glucose levels as a function of time in animals provided the indicated regimen. A significant improvement in the GTT test was observed in AGS treated mice.
Figure 3B:
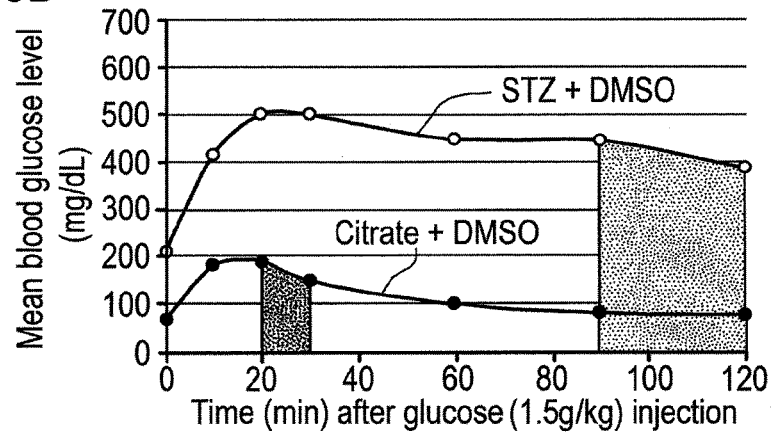
Figure 3C:
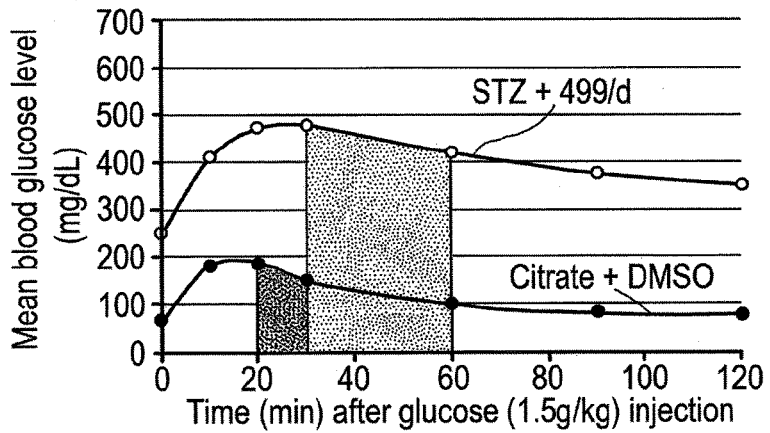
Figure 3D:
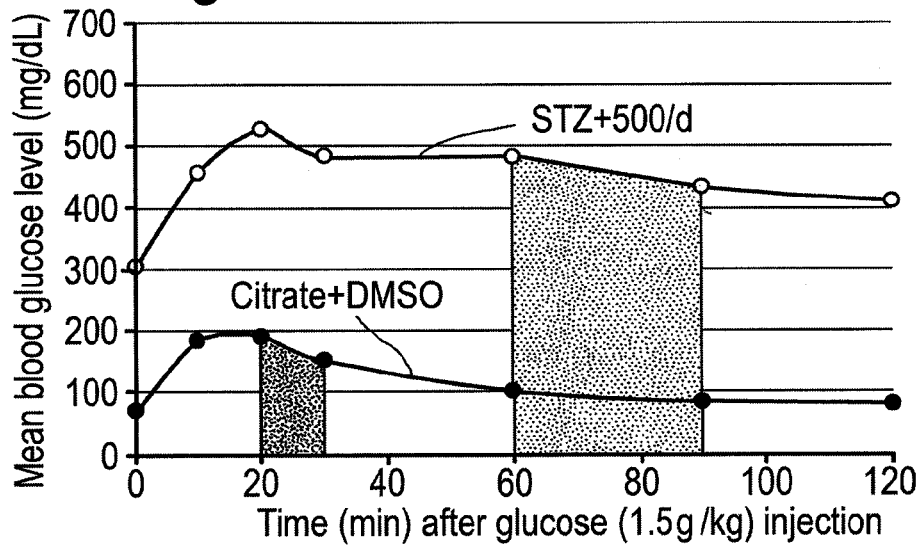
Figure 3E:
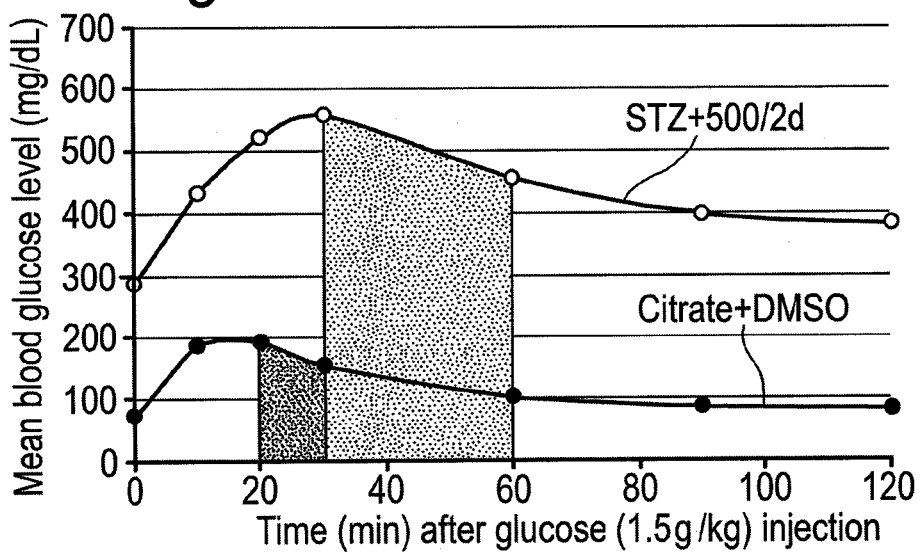
Figure 4A:
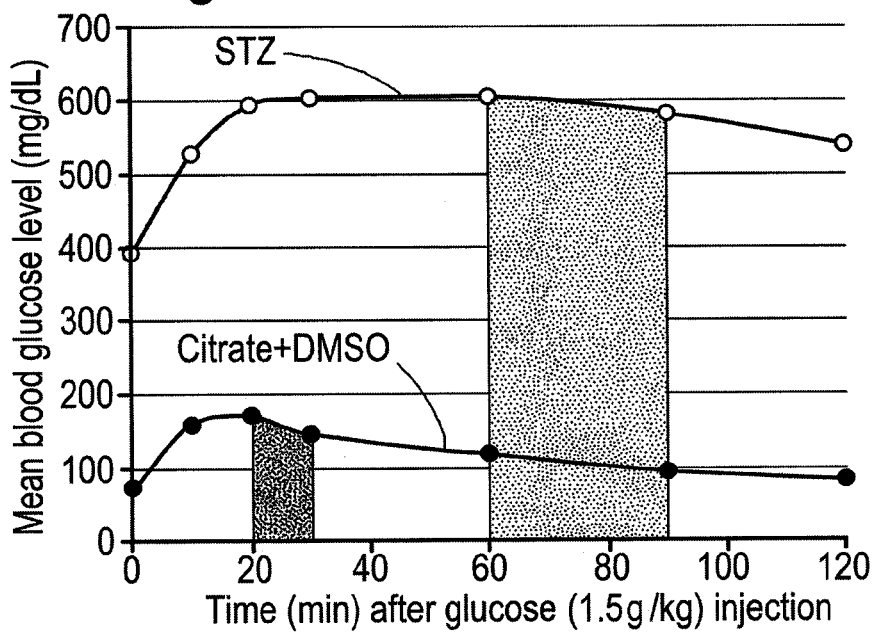
FIGS. 4A-4E: Results of GTT test performed after 5 months showing the mean circulating glucose levels as a function of time in animals provided the indicated regimen. A significant improvement in the GTT test was observed in AGS treated mice in AGS-500 treatment (every 48 hrs) The GTT resemble the GTT in the non-diabetic mice although the level of blood glucose was still very high.
Figure 4B:
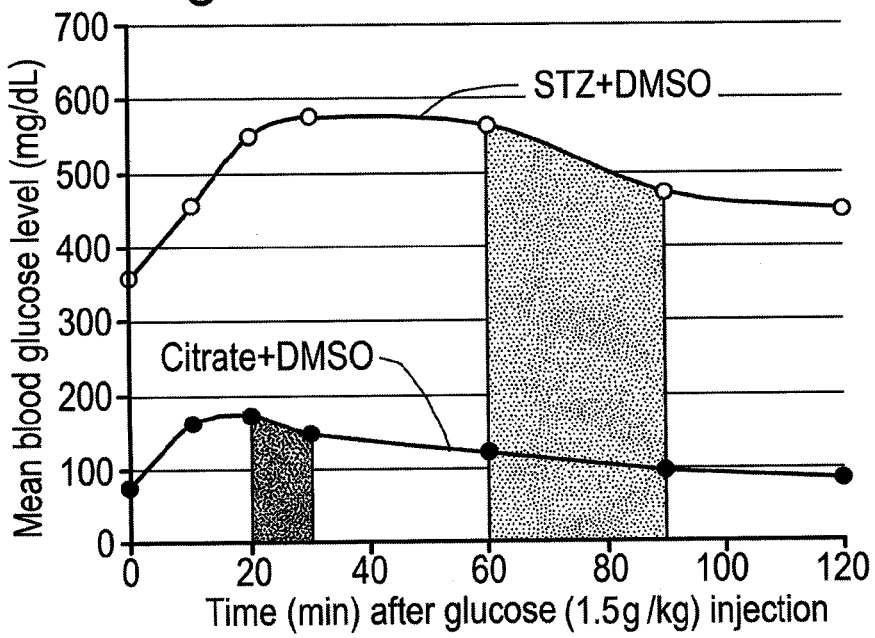
Figure 4C:
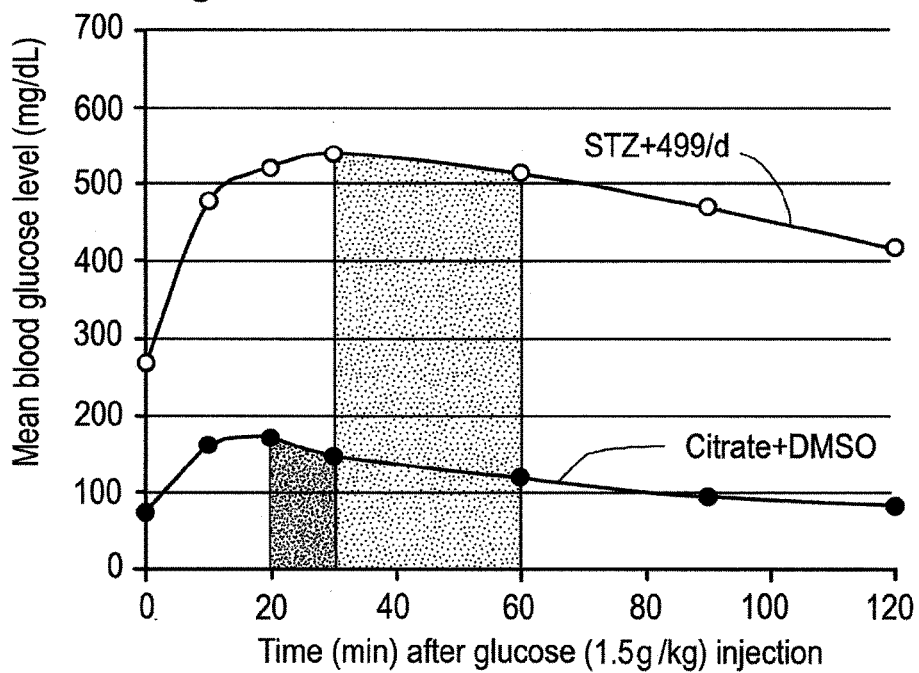
Figure 4D:
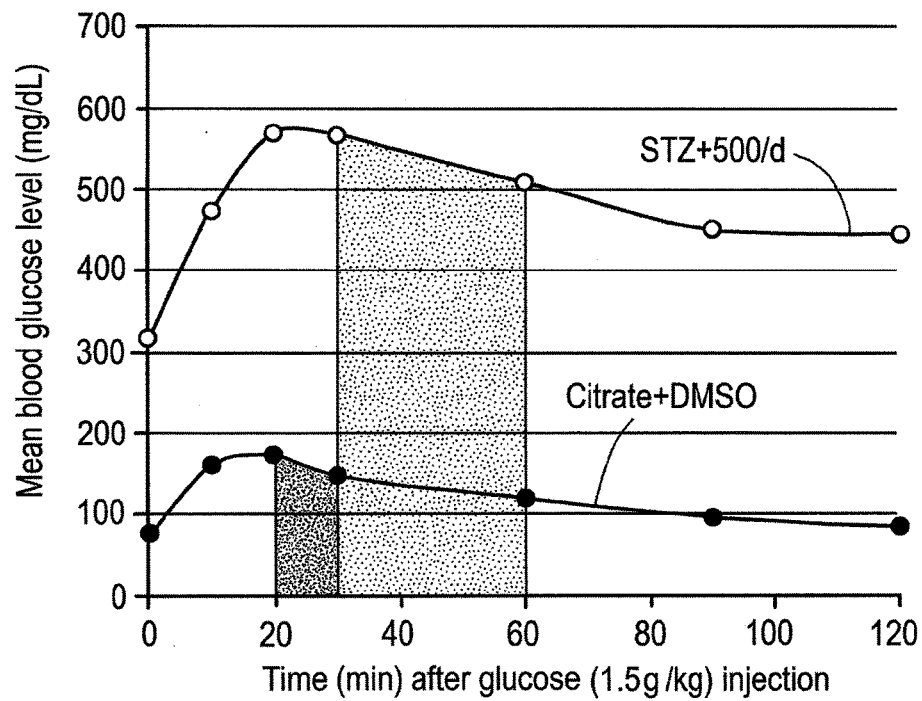
Figure 4E:
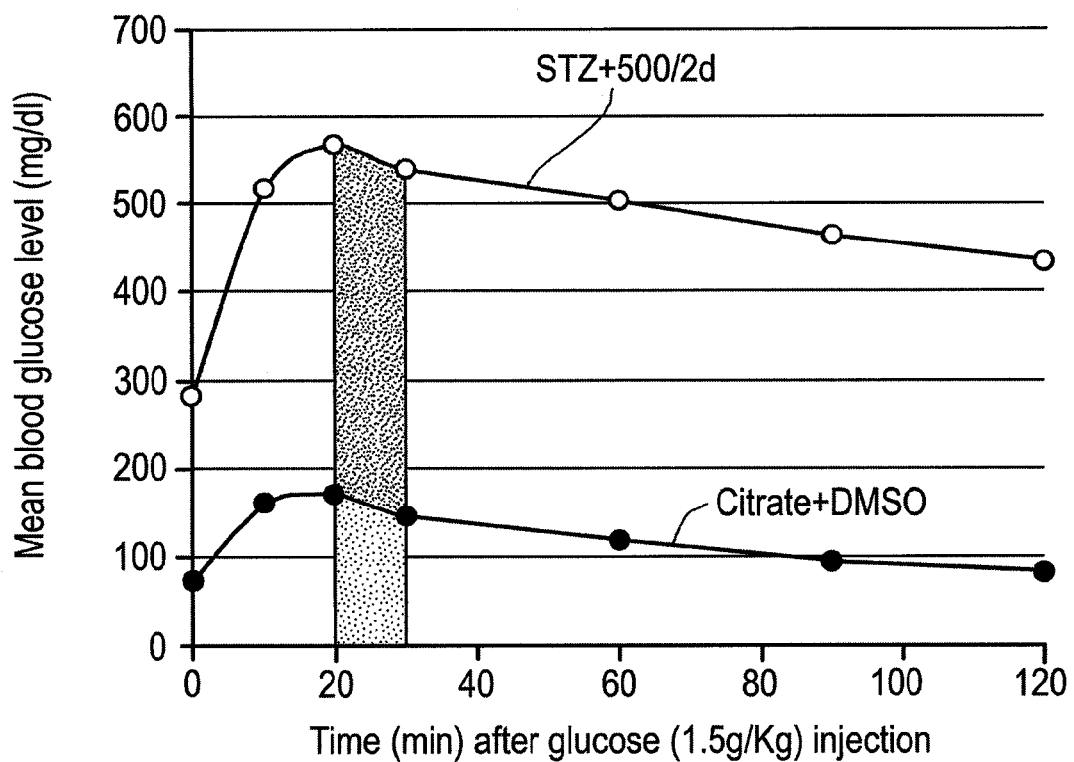
Figures 1, 5A:
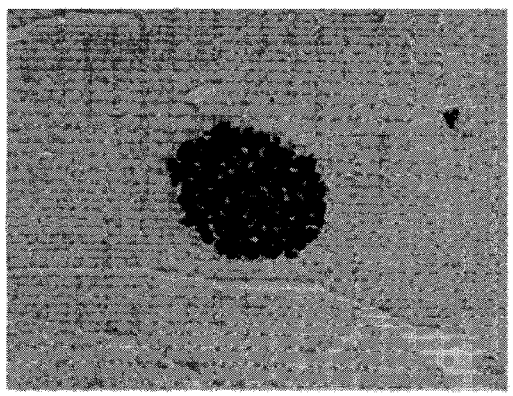
Figures 2, 5A:
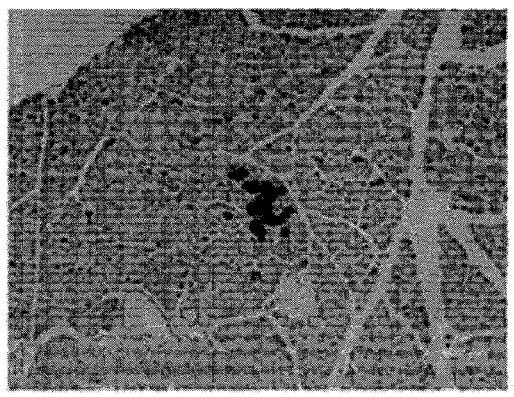
Figures 3, 5A:
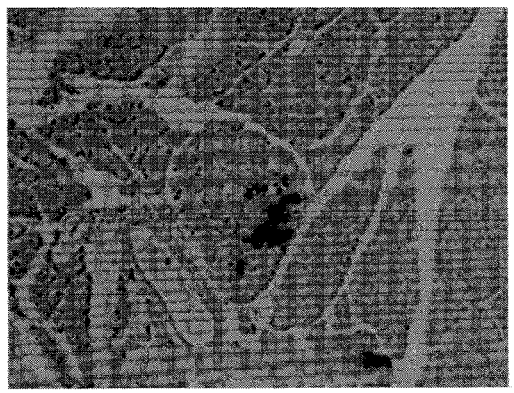

Glucose tolerance tests also revealed a therapeutic effect of AGS-compound treatment (FIG. 3). In glucose tolerance tests (GTT) performed after 2 months, significant improvement in the GTT test was observed in AGS treated mice (FIGS. 3C-3E) as compared to controls (FIGS. 3A-3B). In glucose tolerance tests (GTT) performed after 5 months of AGS or placebo treatment every 48 hours, significant improvement in the GTT test was observed in AGS treated mice (FIGS. 4C-4E) as compared to controls (FIGS. 4A-4B), resembling non-diabetic mice, although the circulating glucose levels were still elevated.

A significant reduction (20-32%) in blood glucose level in the AGS treated diabetic mice after a fast of 12 hours is observed on day 142 (Table 1).

| treatment | Blood glucose level Average | % reduction in blood glucose level |
|---|---|---|
| STZ diabetic rat | 395 | |
| STZ + vehicle | 395 | |
| STZ + AGS499 daily | 317 | 20 |
| STZ + AGS500 daily | 317.4 | 20 |
| STZ + AGS 500 every 48 hrs | 270 | 32 |

A significant reduction in the blood glucose level of 43% is observed in AGS treated diabetic mice after 111 days of treatment. Treatment of AGS compounds alone reduced the blood glucose level to the same values as with insulin+AGS (Table 2).

| insulin | treatment | Blood Glucose At 101 day | % reduction In blood Glucose 101 day | Blood Glucose At 111 day | reduction In blood Glucose 111 day |
|---|---|---|---|---|---|
| no | STZ | 700 | | 600 | |
| no | STZ + vehicle | 700 | | 600 | |
| no | AGS 499 daily | 500 | 29 | 500 | 17% |
| no | AGS 500 daily | 600 | 15 | 450 | 25% |
| no | AGS 500 48 hrs | 400 | 43 | 390 | 35% |
| yes | STZ | 700 | | 600 | |
| yes | STZ + vehicle | 700 | | 600 | |
| yes | AGS499 daily | 480 | 32 | 400 | 34% |
| yes | AGS500 daily | 460 | 34 | 400 | 34% |
| yes | AGS500 48 hrs | 480 | 32 | 400 | 34% |

AGS treated diabetic mice demonstrate a significant improvement in the ability of the pancreas to cope with high glucose load (Table 3).

| Treatment | Time needed for the Pancreas to cope with glucose load after 2 months | Improvement (fold) | Time needed for the Pancreas to cope glucose load after 5 months | Fold of Improvement |
|---|---|---|---|---|
| STZ | 90 min | | 90 min | |
| STZ + DMSO | 90 min | | 60 min | |
| STZ + AGS 499 daily | 30 min | 3 | 30 min | 3 |
| STZ + AGS 500 daily | 60 min | 1.5 | 30 min | 3 |
| STZ + AGS 500/48 hrs | 30 min | 3 | 20 min | normal |
| None diabetic mice | 20 min | normal | 20 min | normal |

AGS Preserved or Increased the Mass of Beta Islets (by 165-215%) in Diabetic Mice.

Immunofluorescence analysis of pancreatic slices derived from the various treated mice; stained with anti-insulin antibody revealed a significant increase in the number of insulin expressing islets in AGS-treated diabetic mice without insulin treatment. Insulin alone demonstrates a 125% increase and disturbed the beneficial effects of AGS compounds (Table 4).

| Treatment | insulin | No of insulin expressing beta islets/mouse | increase in Insulin expressing Beta islets |
|---|---|---|---|
| STZ + DMSO | no | 2.6 | |
| STZ + AGS-499 daily | no | 4.3 | 165% |
| STZ + AGS500 daily | no | 5.6 | 215% |
| STZ + AGS500/48 hrs | no | 5 | 192% |
| STZ − DMSO | yes | 3.25 | 125 |
| STZ + AGS-499 daily | yes | 3.5 | 135% |
| STZ + AGS500 daily | yes | 2.5 | — |
| STZ + AGS500/48 hrs | yes | 3 | 115% |

Example 2

Compounds of this Invention Increase Pancreatic Beta Cell Mass

Rats were treated as described in Example 1, pancreata were removed fixed in 4% formalin, and embedded in paraffin for immuno-histochemical and immuno-fluorescence staining using a specific anti-insulin antibody and serial histopathologic sections were prepared.

Figures 4, 5A:
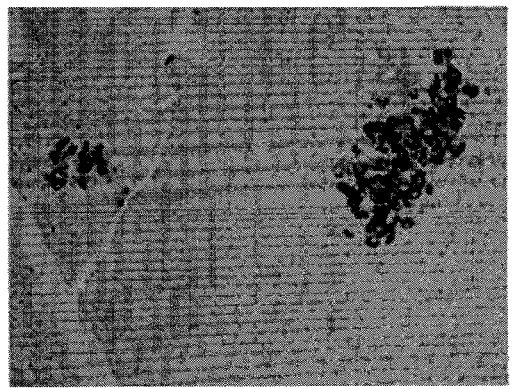
Figures 1, 5B:
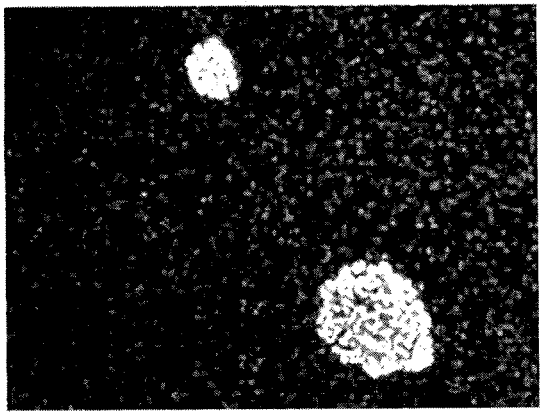
Figures 2, 5B:
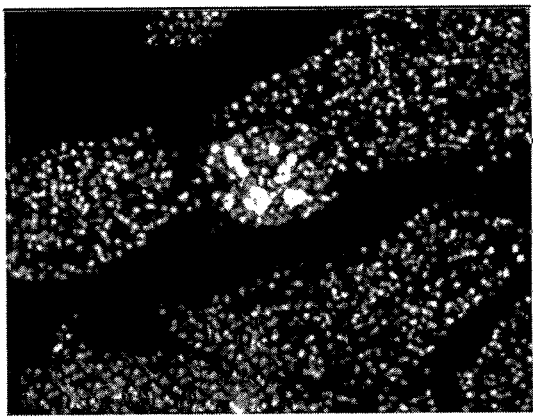
Figures 3, 5B:
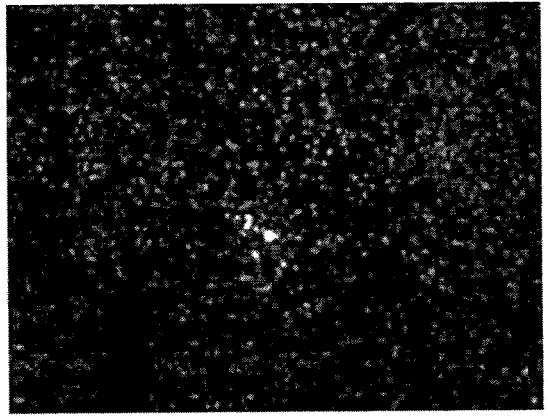
Figures 4, 5B:
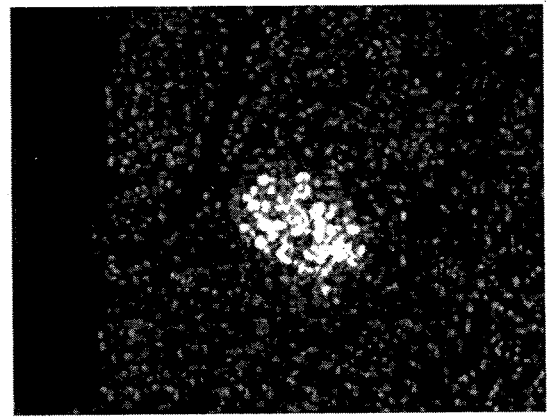
Figures 3, 6A:
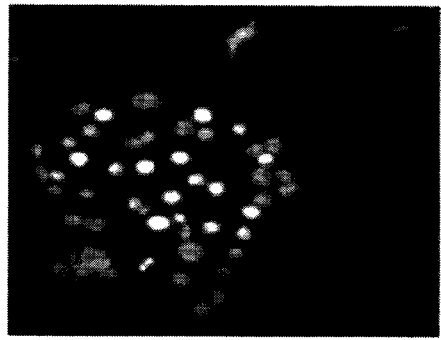
Figures 2, 6A:
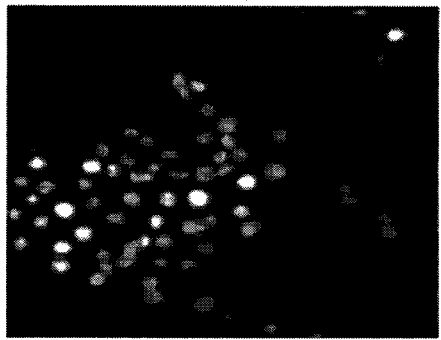
Figures 1, 6A:
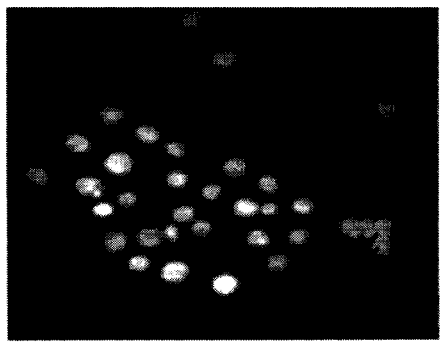
Figures 5, 6A:
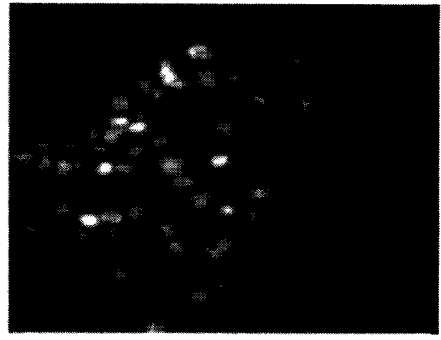
Figures 4, 6A:
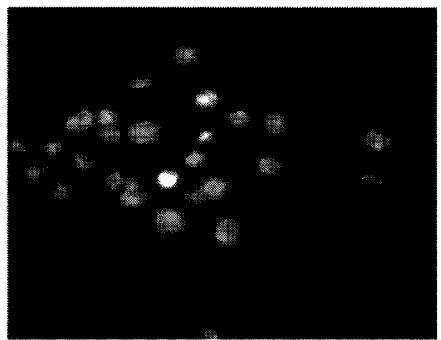

Immuno-histochemical and immuno-fluorescence insulin-staining demonstrated the presence of a significantly larger β-cell mass in the pancreas of AGS-500-treated rats compared to untreated or vehicle-treated rats, in which significant destruction of β-cells was observed (FIG. 5). Brown staining in FIG. 5A indicates insulin staining positivity by immunohistochemistry, and red staining (FIGS. 5B and 5C) indicates insulin staining positivity by immunofluorescence, blue cellular staining was effected with Dapi). The Cell density and density of insulin staining per area was measured using "Image J" software (FIGS. 5D and 5E). The results are presented as mean±S.E.; n=4. ***p<0.005.

The treatment of rats with AGS-compounds maintained a large β-cell mass in STZ-treated rats. In order to determine whether β-cell mass preservation was a result islet cell protection from STZ-induced DNA damage, γ-H2AX staining was assessed. Phosphorylated gamma H2AX (γ-H2AX) is essential for recognition and repair of DNA double strand breaks. H2AX histone becomes rapidly phosphorylated at its carboxyl terminus to form the so-called γ-H2AX at double strand break sites.

Figures 4, 12:
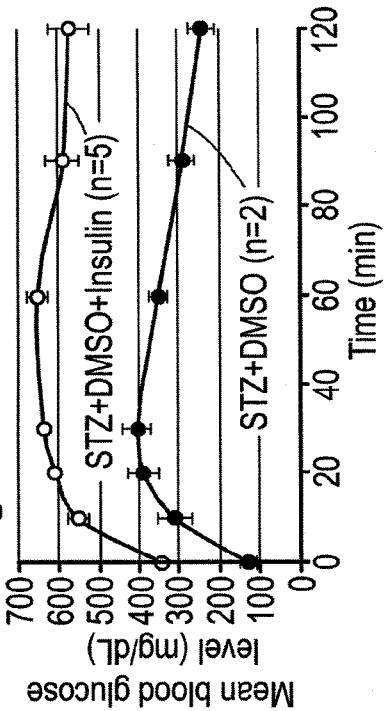
Figures 6, 12:
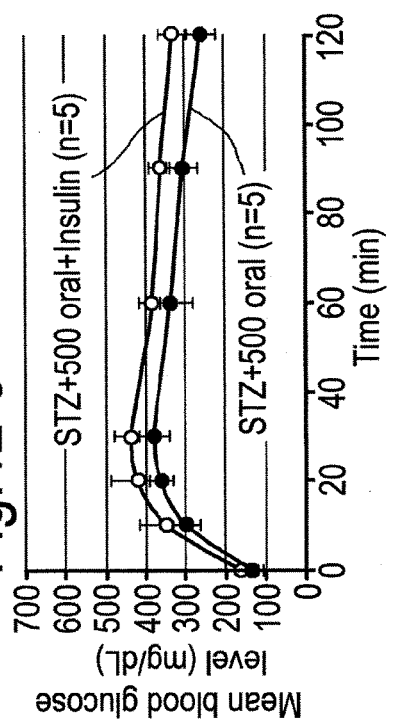
Figures 3, 12:
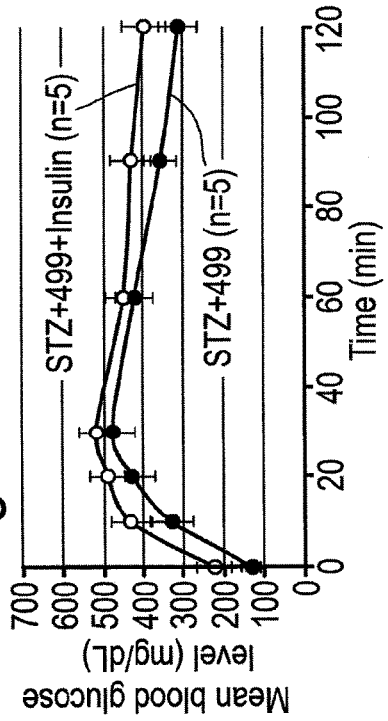
Figures 5, 12:
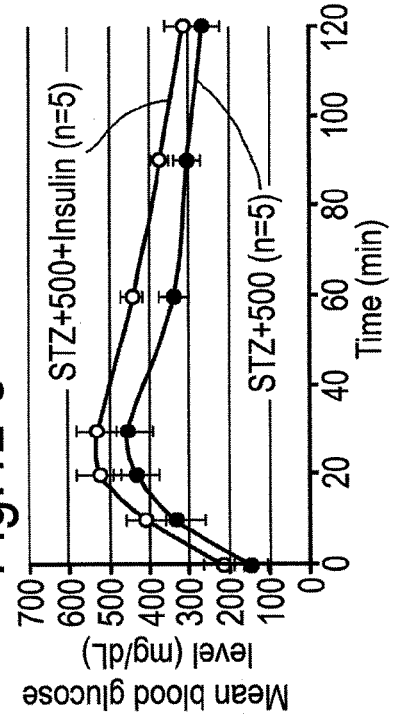

Islets were isolated from 8-10-week-old ICR mice and were treated with STZ (1.5 mM) and DMSO or AGS-500 in various concentrations (50 nM, 100 nM, 250 nM) for 4 hours. After a 4 h incubation, the islets were separated into single cells, cyto-spun, and stained with anti-γ-H2AX-specific antibody for the detection of DNA double strand breaks (FIG. 6). A dose-dependent decrease in the number of γ-H2AX-stained cells after treatment with 250 nM AGS-500, as compared to control samples.

Beta cells islets isolated from rats pancreata treated with STZ and AGS compounds at various concentrations show increased viability, as determined by OD (FIG. 7).

Example 3

Compounds of this Invention Treat Disease Conditions Arising as a Consequence of Diabetes: Improved Kidney Function Mice were treated as described hereinabove. Following one month of treatment mice were sacrificed and histolopathological examination of the kidney was performed.

Periodic acid-Schiff (PAS) staining of kidney slices indicated that the glomerulus derived from the diabetic animal (designated STZ or STZ-DMSO) exhibit a damaged phenotype while the glomerulus derived from diabetic animal treated with AGS exhibited a normal phenotype similarly to non-diabetic animals (FIG. 8). The total number of normal glomeruli in the AGS treated diabetic mice was significantly higher compared to the diabetic untreated mice.

AGS treatment also decreased carbohydrate precipitation in afferent blood vessels. FIG. 8-6 shows the afferent blood vessel in a normal mouse (non-diabetic, see arrow), while there is significant carbohydrate preceiption in untreated diabetic mice (see FIGS. 8-8 and 8-9, arrow). FIG. 8-7 shows a reduction in the carbohydrate precipitation in the afferent vessel in AGS treated mice (arrow).

Figure 9:
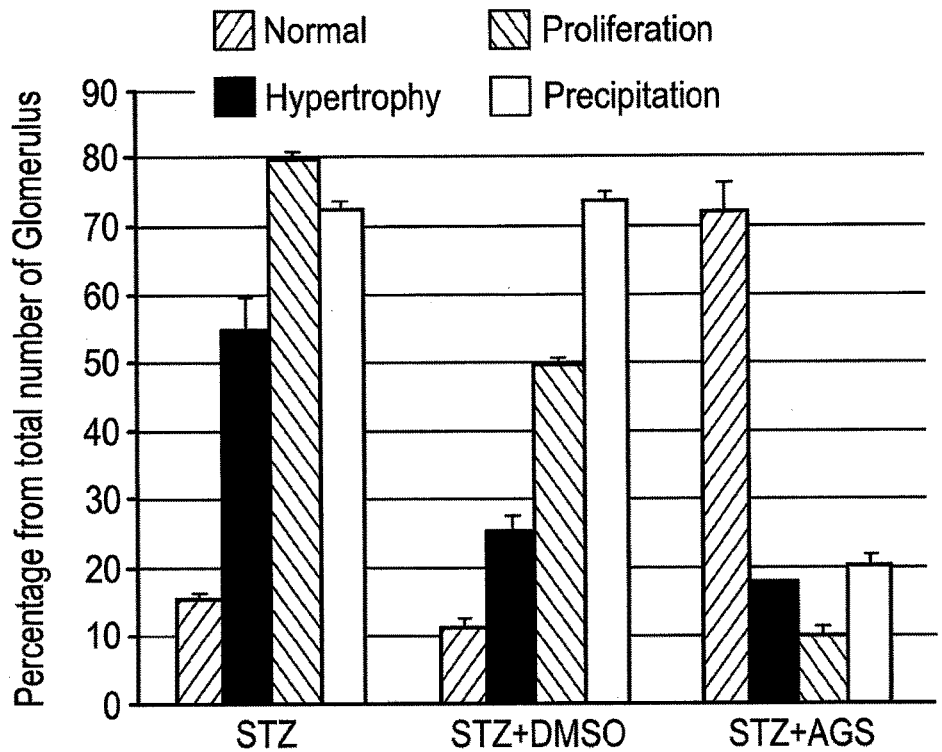
FIG. 9 plots parameters assessed via histopathology analysis of glomeruli in AGS treated diabetic animals, as compared to controls.

FIG. 9 plots the evaluation of a number of parameters assessed via the histopathology analysis. The number of normal glomeruli versus the number of glomeruli exhibiting tissue damage was established, including hypertrophy, proliferation, precipitation or fibrosis (N=2.3).

AGS treatment significantly improved each parameter, as compared to controls.

The glomerular filtration rate of diabetic mice after treatment with AGS compounds was evaluated, as a measure of kidney function. At least 4 STZ-induced diabetic ICR mice each per group were injected with AGS compounds (6 mg/kg) or DMSO (serving as controls) for 5 months for evaluation of creatinine clearance, by determining creatinine levels in urine and serum samples from the respective groups. Results represent means±SE. *p<0.05. n≥4.

Figure 10:
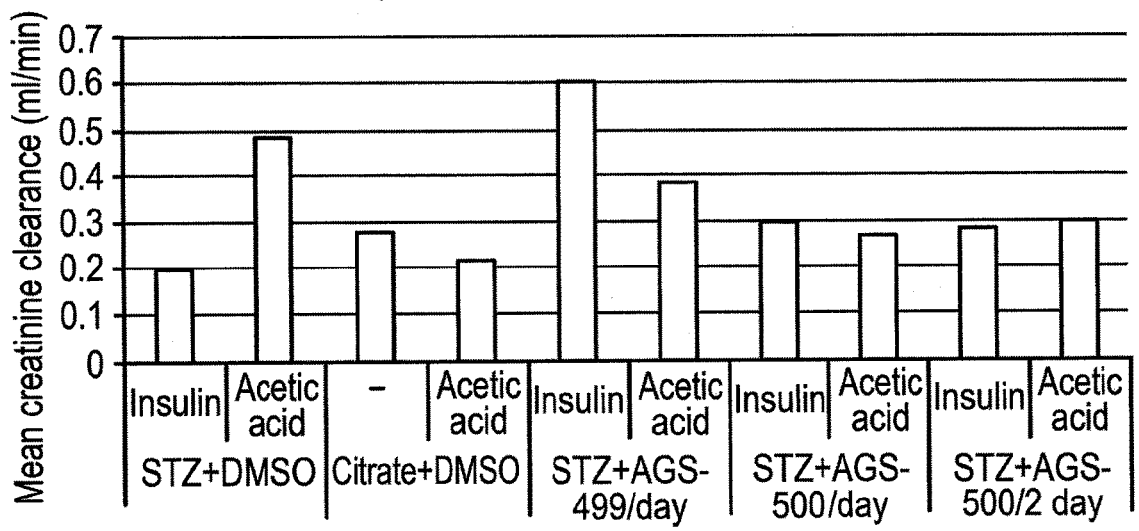
FIG. 10 plots the kidney function improvement in STZ-induced diabetes as a function of reduced creatinine clearance rate to normal levels in diabetic mice treated with AGS compounds, as compared to controls.

Kidney function improvement in STZ-induced diabetes was evidenced by improved glomerular filtration rates in AGS treated mice as compared to controls (FIG. 10).

Example 4

Compounds of this Invention Help Maintain Lower Circulating Glucose Levels Over Time Eight weeks-old female ICR mice were injected intraperitoneally (IP) with Streptozotocin (STZ), at a dose of 40 mg/Kg, for 5 consecutive days. The following day and onward, mice were administered the AGS compounds (499 or 500, as indicated), at a dose of 6 mg/Kg, either subcutaneously or orally, every other day. Blood glucose levels were monitored daily.

After the establishment of diabetes (i.e. three consecutive blood glucose measurements of >200 mg/dL), mouse groups were further sub-divided into 2 sub-groups, one of each received insulin (gradual administration of 0.5-6 units/Kg, over a period of 2 weeks) subcutaneously, every other day. Blood glucose levels were monitored daily.

Glucose tolerance tests were also performed as follows: After two weeks mice were fasted for 12 hours, then injected with D-glucose (1.5 g/Kg, IP) and blood glucose levels were examined at 0, 10, 20, 30, 60, 90 and 120 minutes, in order to evaluate pancreatic function.

Figures 2, 11:
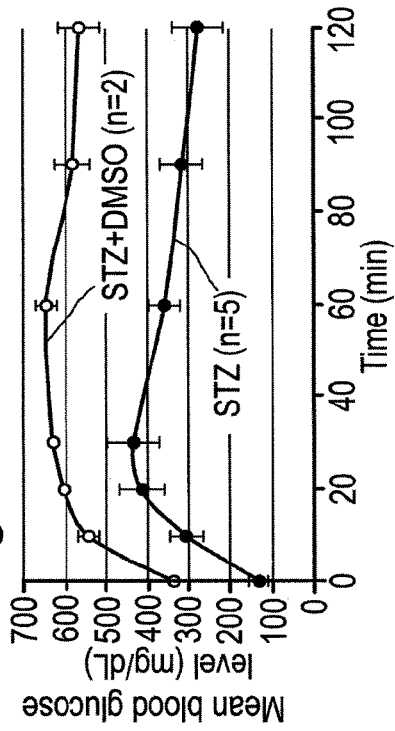
Figures 4, 11:
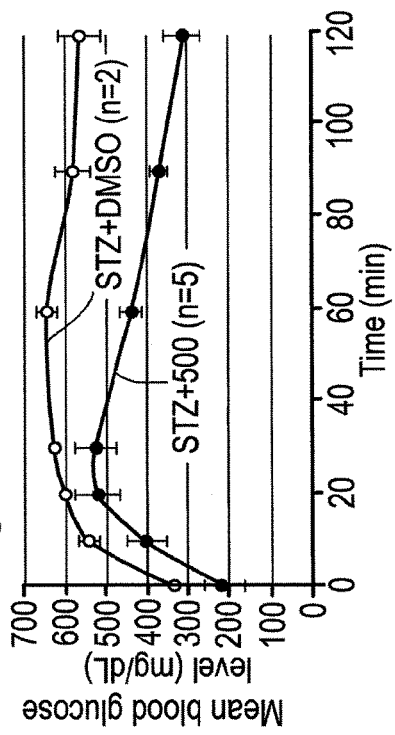
Figures 1, 11:
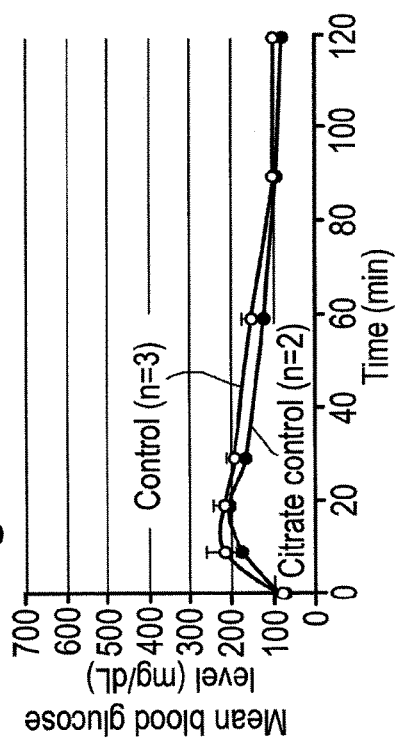
Figures 3, 11:
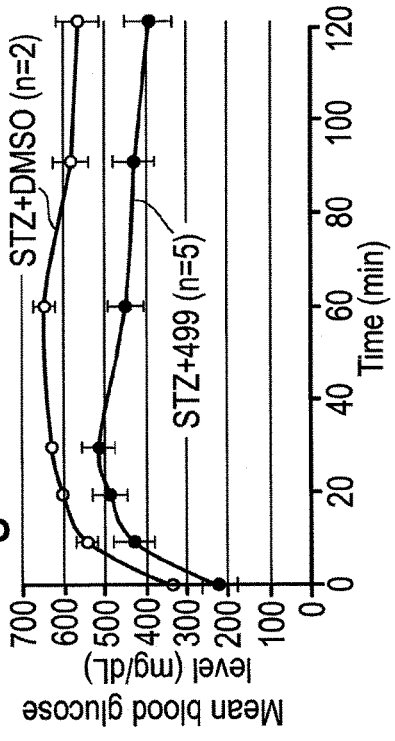

AGS treatment with and without concomitant insulin treatment reduced mean blood glucose levels in a glucose tolerance test (FIG. 11, compare 11-3 and 11-5 and 11-4 and 11-6 versus 11-2, for example, showing the effects of AGS499 and AGS500, respectively, in lowering circulating glucose levels, when given subcutaneously or orally.

It was of interest to determine whether subjects may in fact reduce or refrain from insulin administration, i.e. would the AGS 499 or AGS 500 compounds alone be sufficient. FIG. 12 plots the combined effect in glucose lowering capacity of either compound alone or in combination with insulin administration in a glucose tolerance test setting. As can be seen in FIGS. 12-2, 12-3 and 12-5 versus FIG. 12-4, for example, showing the effects of AGS499 and AGS500, respectively, in lowering circulating glucose levels in a glucose tolerance test, when given subcutaneously, and in the case of AGS500 when also given orally, adding insulin did not appreciably lower the circulating levels.

Figures 2, 2G:
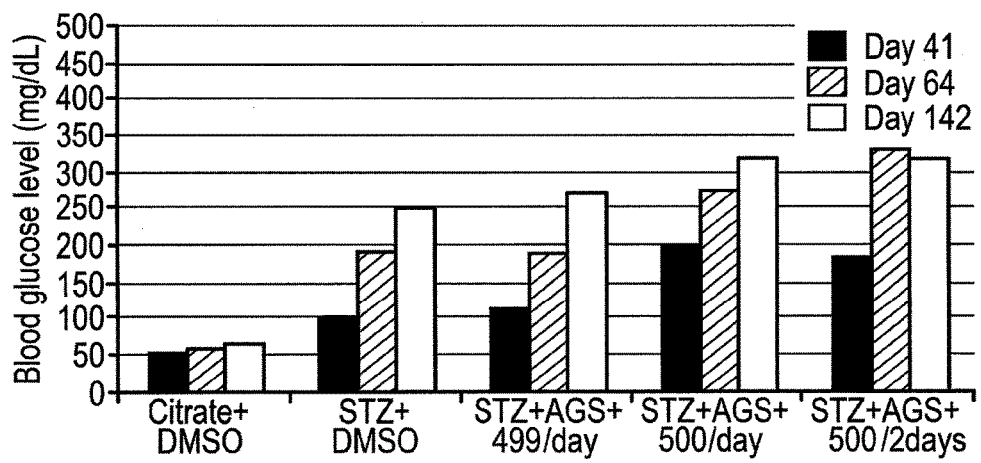
Figures 1, 13:
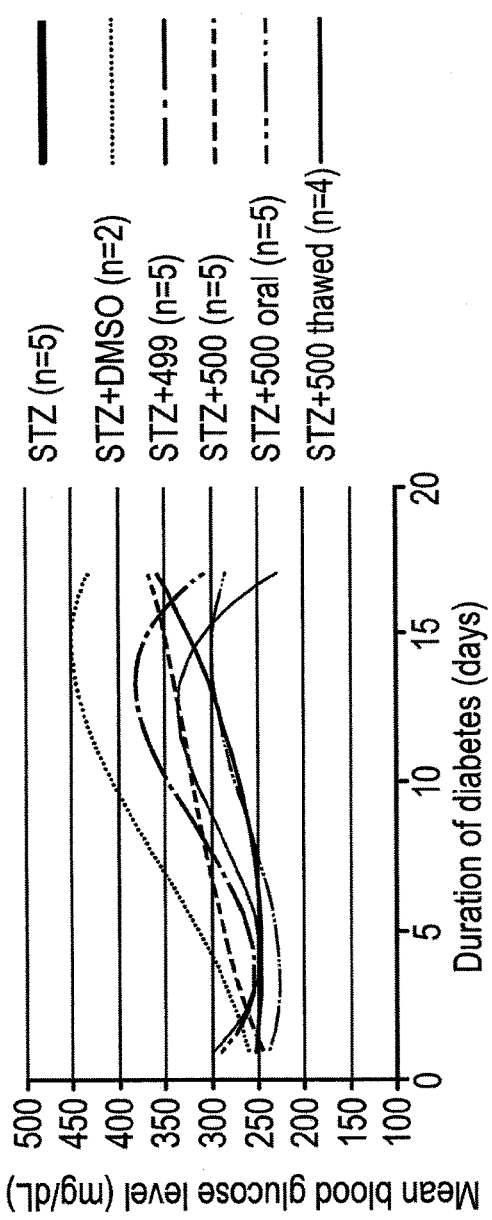
Figures 2, 13:
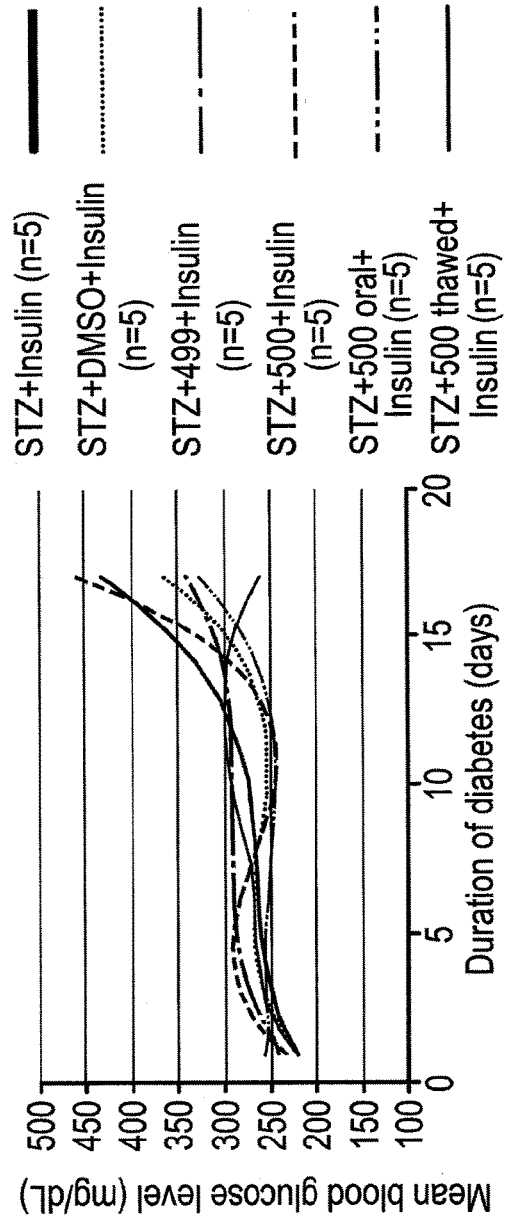

FIG. 13 displays the results of the combination therapy in lowering circulating glucose levels (after a short treatment time) over time. FIG. 13-1 shows the efficacy of AGS-499 or AGS-500 lowering circulating glucose levels significantly, even more than 15 days out. FIG. 13-2 shows the synergistic contribution when both AGS-499 or AGS-500 is combined with insulin therapy.

Uniquely, in these aspects, treatment with the AGS compounds for only two weeks, on day one following STZ injection shows marked reduction in blood glucose levels. Previous Examples show an effect, with the AGS compounds, as well, in long-term therapy settings, after the establishment of high blood glucose levels in the treated subjects.

Taken together, the invention as described and exemplified herein shows a series of compounds reducing circulating glucose levels in diabetic subjects, reversing organ damage arising as a result of diabetes, and providing short- and long-term therapeutic potential in diabetic subjects, including improving pancreatic islet beta cell mass impacting both disease progression and overall pathogenesis.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of treating diabetes or diabetes related complications in a subject in need thereof, said method comprising administering to a subject an effective amount of a compound represented by the structure of formula I:

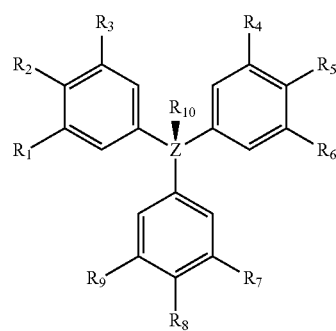

wherein

Z is carbon, phosphorus, or nitrogen;

$R_1$, $R_3$, $R_4$, $R_6$, $R_7$ and $R_9$ are the same or different H, halogen, halo$C_{1-6}$alkyl, aryl, $C_{1-6}$alkyl, cyclo$C_{1-6}$alkyl, heterocyclo$C_{1-6}$alkyl, $C_{1-6}$alkoxy, mono$C_{1-6}$alkylamino, di$C_{1-6}$alkylamino or arylamino;

$R_2$, $R_5$ and $R_8$ are the same or different H, halogen OH, $C_{1-6}$alkyl, or $C_{1-6}$alkoxy; and $R_{10}$ is nothing when Z is phosphorous or nitrogen, and OH or $C_{1-6}$alkyl when Z is carbon.

2. A method of reducing circulating glucose levels, reducing insulin resistance, stimulating or increasing insulin sensitivity, stimulating or increasing pancreatic beta-cell mass, or stimulating or increasing creatinine clearance in a subject in need thereof, or reducing renal damage in a diabetic subject in need thereof, said method comprising administering to a subject an effective amount of a compound represented by the structure of formula I:

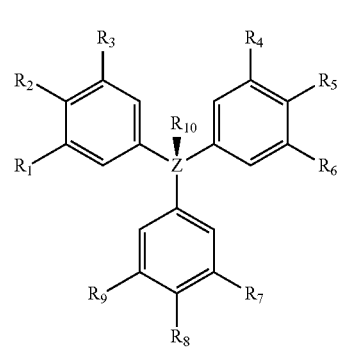

wherein

Z is carbon, phosphorus, or nitrogen;

$R_1$, $R_3$, $R_4$, $R_6$, $R_7$ and $R_9$ are the same of different H, halogen, halo$C_{1-6}$alkyl, aryl, $C_{1-6}$alkyl, cyclo$C_{1-6}$alkyl, heterocyclo$C_{1-6}$alkyl, $C_{1-6}$alkoxy, mono$C_{1-6}$alkylamino, di$C_{1-6}$alkylamino or arylamino;

$R_2$, $R_5$ and $R_8$ are the same or different H, halogen, OH, $C_{1-6}$alkyl, or $C_{1-6}$alkoxy; and $R_{10}$ is nothing when Z is phosphorous or nitrogen, and OH or $C_{1-6}$alkyl when Z is carbon.

3. The method of claim 1, wherein said compound is represented by the structure of formula II:

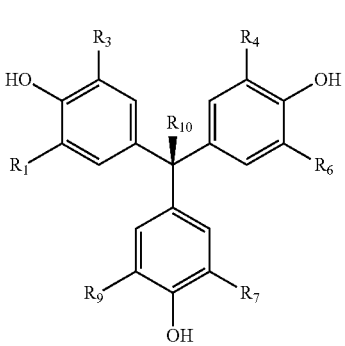

wherein $R_1$, $R_3$, $R_4$, $R_6$, $R_7$, $R_9$ and $R_{10}$ are as described above.

4. The method of claim 3, wherein said compound is represented by the structure of formula VI:

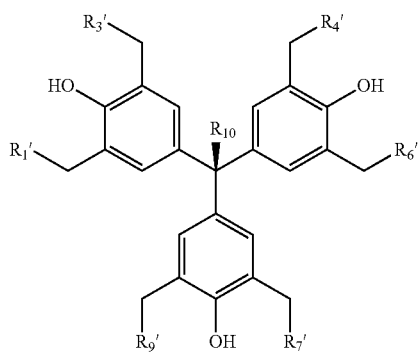

wherein $R_1'$, $R_3'$, $R_4'$, $R_6'$ $R_7'$, and $R_9'$ are the same or different comprising halogen, halo$C_{1-6}$alkyl, aryl, $C_{1-6}$alkyl, cyclo$C_{1-6}$alkyl, heterocyclo$C_{1-6}$alkyl, $C_{1-6}$alkoxy, mono$C_{1-6}$alkylamino, di$C_{1-6}$alkylamino or arylamino; and $R_{10}$ is as described above.

5. The method of claim 4, wherein said compound is represented by the structure of formula VII:

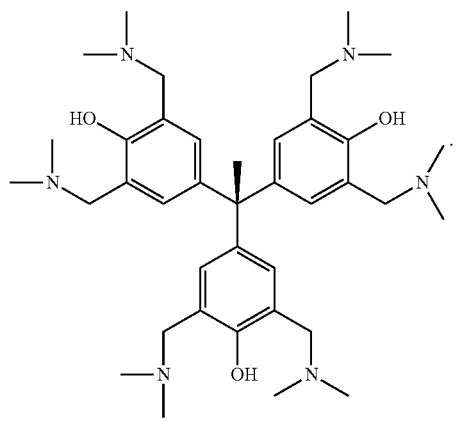

6. The method of claim 4, wherein said compound is represented by the structure of formula VIII:

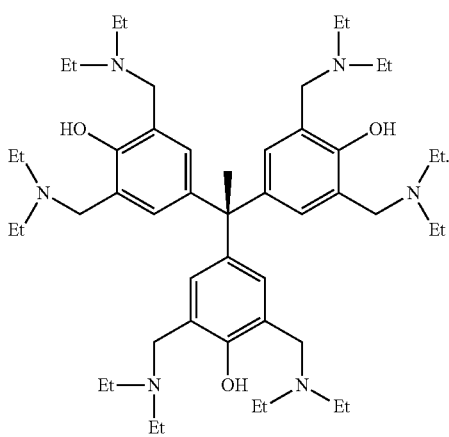

7. The method of claim 4, wherein said compound is represented by the structure of formula IX:

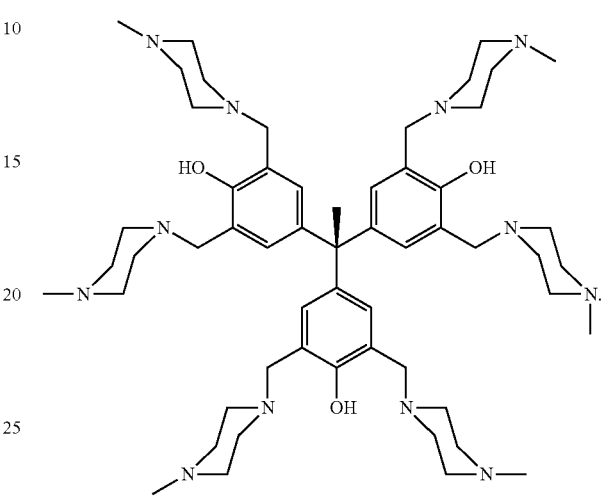

8. The method of claim 4, wherein said compound is represented by the structure of formula X:

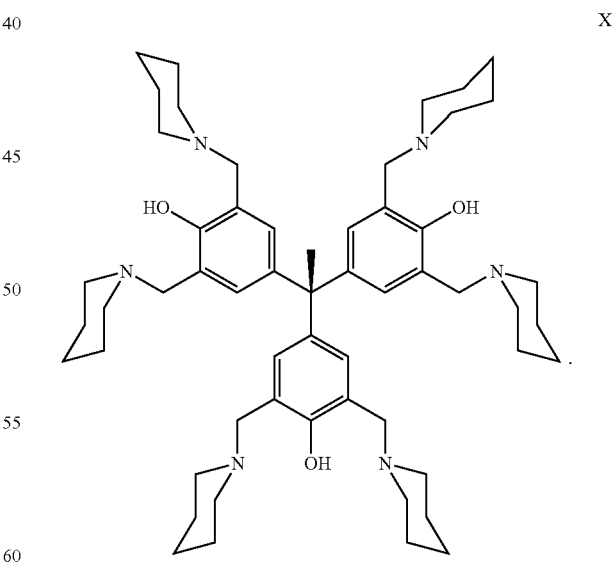

9. The method of claim 4, wherein said compound is represented by the structure of formula XI:

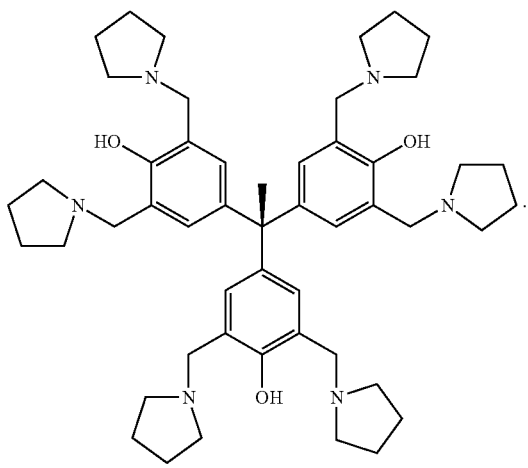

10. The method of claim 4, wherein said compound is represented by the structure of formula XII:

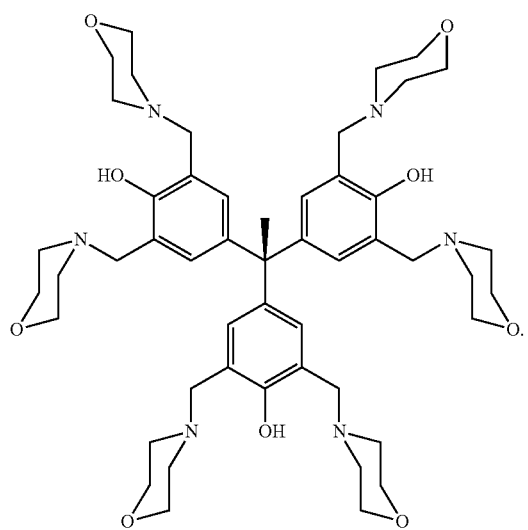

11. The method of claim 4, wherein said compound is represented by the structure of formula XIII:

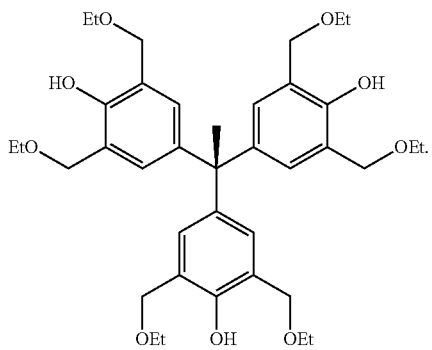

12. The method of claim 1, wherein said compound is represented by the structure of formula XIV:

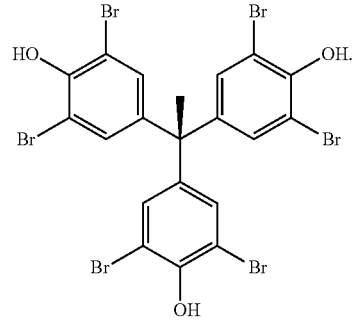

13. The method of claim 1, wherein said compound is represented by the structure of formula XV:

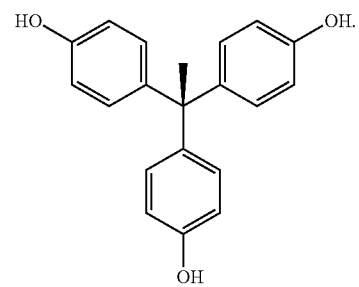

14. The method of claim 1, wherein said compound is represented by the structure of formula XVI:

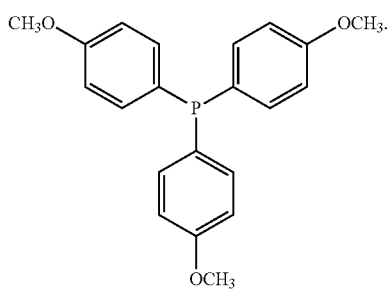

15. The method of claim 1, wherein said subject is administered a second agent, which is useful in the treatment of diabetes or diabetes related complications.

16. The method of claim 1, wherein said subject is administered a second agent, which is useful in the reduction of circulating glucose levels, reduction of insulin resistance, stimulation or increase of insulin sensitivity, stimulation or increase of pancreatic beta-cell mass, or stimulation or increase of creatinine clearance in a subject, or reduction of renal disease in said subject.

17. The method of claim 1, wherein $R_1$, $R_3$, $R_4$, $R_6$, $R_7$ and $R_9$ are the same and independently $R_2$, $R_5$ and $R_8$ are the same.

18. The method of claim 2, wherein $R_1$, $R_3$, $R_4$, $R_6$, $R_7$ and $R_9$ are the same and independently $R_2$, $R_5$ and $R_8$ are the same.

19. The method of claim 17, wherein Z is carbon, $R_2$, $R_5$ and $R_8$ are OH, and $R_{10}$ is $C_{1-4}$alkyl.

20. The method of claim 19, wherein $R_{10}$ is methyl.

21. The method of claim 18, wherein Z is carbon, $R_2$, $R_5$ and $R_8$ are OH, and $R_{10}$ is $C_{1-4}$alkyl.

22. The method of claim 21, wherein $R_{10}$ is methyl.

* * * * *